(12) United States Patent
Burkamp et al.

(10) Patent No.: US 8,338,587 B2
(45) Date of Patent: Dec. 25, 2012

(54) COMPOUNDS

(75) Inventors: Frank Burkamp, Södertälje (SE); Peter Hansen, Lund (SE); Balint Gabos, Lund (SE); Håkan Bladh, Lund (SE)

(73) Assignee: AstraZeneca AB, Sodertalje ( * ) Notice: Subject to any disclaimer, the term of this patent is extended or adjusted under 35 U.S.C. 154(b) by 139 days.

(21) Appl. No.: 12/749,911

(22) Filed: Mar. 30, 2010

(65) Prior Publication Data

US 2010/0256103 A1    Oct. 7, 2010

Related U.S. Application Data

(60) Provisional application No. 61/166,325, filed on Apr. 3, 2009.

(51) Int. Cl.
*C07D 345/00* (2006.01)

(52) U.S. Cl. ............... 540/1; 514/171; 514/176; 540/53

(58) Field of Classification Search .................. 514/171, 514/176; 540/53
See application file for complete search history.

(56) References Cited

U.S. PATENT DOCUMENTS

| | | | |
|---|---|---|---|
| 3,072,639 A | 1/1963 | Hirschmann et al. | |
| 3,129,218 A | 4/1964 | Fried et al. | |
| 3,364,203 A | 1/1968 | Beard et al. | |
| 3,471,477 A | 10/1969 | Fried | |
| 4,242,334 A | 12/1980 | Stache et al. | |
| 4,377,575 A | 3/1983 | Stache et al. | |
| 4,820,700 A | 4/1989 | Brattsand et al. | |
| 2009/0286835 A1 | 11/2009 | Bladh et al. | |
| 2010/0256104 A1 | 10/2010 | Burkamp et al. | |
| 2010/0256105 A1 | 10/2010 | Burkamp et al. | |
| 2010/0261690 A1 | 10/2010 | Burkamp et al. | |
| 2011/0262368 A1 | 10/2011 | Anthes et al. | |

FOREIGN PATENT DOCUMENTS

| | | |
|---|---|---|
| DE | 2727367 A1 | 1/1979 |
| EP | 0000471 A1 | 2/1979 |
| GB | 933867 A | 8/1963 |
| JP | 60067495 A | 5/1985 |
| WO | WO-94/25478 A1 | 11/1994 |
| WO | WO-97/22596 A1 | 6/1997 |
| WO | WO-97/30035 A | 8/1997 |
| WO | WO-97/32856 A | 9/1997 |
| WO | WO-98/13354 A | 4/1998 |
| WO | WO-99/02166 A1 | 1/1999 |
| WO | WO-00/40529 A1 | 7/2000 |
| WO | WO-00/41669 A2 | 7/2000 |
| WO | WO-01/92224 A1 | 12/2001 |
| WO | WO-02/04434 A1 | 1/2002 |
| WO | WO-02/08213 A1 | 1/2002 |
| WO | WO-02/088167 A1 | 11/2002 |
| WO | WO-02/088169 A2 | 11/2002 |
| WO | WO-2004/052912 A1 | 6/2004 |
| WO | WO-2005/028495 A1 | 3/2005 |
| WO | WO-2005/063777 A1 | 7/2005 |
| WO | WO-2006/108572 A2 | 10/2006 |
| WO | WO-2007/054974 A2 | 5/2007 |
| WO | WO-2009/044200 A1 | 4/2009 |
| WO | 2009/085880 A8 | 7/2009 |
| WO | WO-2009/082342 A1 | 7/2009 |
| WO | WO-2009/108118 A1 | 9/2009 |
| WO | WO-2010/114471 A1 | 10/2010 |
| WO | WO-2010/114472 A1 | 10/2010 |
| WO | WO-2010/114473 A1 | 10/2010 |

OTHER PUBLICATIONS

Bodor, N.S., et al., "Novel Soft Steroids: Effects on Cell Growth In Vitro and on Wound Healing in the Mouse", *Steroids*, vol. 56, pp. 434-439 (1991).

Sugai, S., et al., "Studies on Topical Antiinflammatory Corticosteroids. III. Synthesis and Vasoconstrictive Activity of 11β,17α,21-Trihydroxy-2'-phenyl-2'H-2,4-pregnadieno[3,2,-c]pyrazol-20-one Derivatives", *Chem. Pharm. Bull.*, vol. 34, No. 4, pp. 1613-1618 (1986).

Hirschmann, R., et al., "Synthesis and Structure of Steroidal 4-Pregneno[3,2-c]Pyrazoles. A Novel Class of Potent Anti-Inflammatory Steroids", *Journal of the American Chemical Society*, vol. 85, pp. 120-122 (1963).

Hoyte, R.M., et al., "Synthesis of Halogen-Substituted Pyridyl and Pyrimidyl Derivatives of [3,2-c]Pyrazolo Corticosteroids: Strategies for the Development of Glucocorticoid Receptor Mediated Imaging Agents", *J. Med. Chem.*, vol. 45, pp. 5397-5405 (2002).

Hoyte, R.M., et al., "Iodinated and Fluorinated Steroid 2'-Aryl-[3,2-c] Pyrazoles as Potential Glucocorticoid Receptor Imaging Agents", *Steroids*, vol. 63, pp. 595-602 (1998).

(Continued)

*Primary Examiner* — Brandon Fetterolf
*Assistant Examiner* — Jean Cornet
(74) *Attorney, Agent, or Firm* — David Gryte

(57) ABSTRACT

The present invention provides named compounds of formula (I)

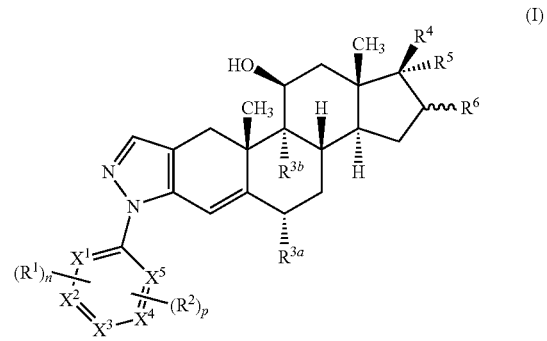

and pharmaceutical compositions containing them and their use in therapy.

7 Claims, No Drawings

OTHER PUBLICATIONS

Hirschmann, R., et al., "Synthesis of Pregn-4-eno[3,2-c]pyrazoles Related to 9α-Fluoro-16a-methylcortisol", *Journal of Medicinal Chemistry*, vol. 7, pp. 352-355 (1964).

Hannah, J., et al., "Substituted Pyrazolo Corticoids as Topical Antiinflammatory Agents", *Journal of Medicinal Chemistry*, vol. 18, No. 2, pp. 168-172 (1975).

Hirschmann, R., et al., "Synthesis and Structure of Steroidal Pregn-4-eno- and 5α-Pregnano [3,2-c]pyrazoles. A Novel Class of Potent Anti-Inflammatory Steroids", *Journal of the American Chemical Society*, vol. 86, pp. 1520-1527 (1964).

Kahn, M.G.C., et al., "Microwave-Enhanced Nucleophilic Fluorination in the Synthesis of Fluoropyridyl Derivatives of [3,2-c]Pyrazolo-Corticosteroids, Potential Glucocorticoid Receptor-Mediated Imaging Agents", *Bioorganic & Medicinal Chemistry Letters*, vol. 16, pp. 3454-3458 (2006).

Loftsson, L., et al., "The Pharmacokinetics and Transdermal Delivery of Loteprednol Etabonate and Related Soft Steroids", *Advanced Drug Delivery Reviews*, vol. 14, pp. 293-299 (1994).

Wuest, F., et al., "Synthesis of Novel Arylpyrazolo Corticosteroids as Potential Ligands for Imaging Brain Glucocorticoid Receptors", *Steroids*, vol. 68, pp. 177-191 (2003).

Tomlinson, J.E.M., et al., "Efficacy of Low and High Dose Inhaled Corticosteroid in Smokers Versus Non-Smokers with Mild Asthma", *Thorax*, vol. 60, pp. 282-287 (2005).

International Search Report of PCT/SE2010/050367, mailed Jul. 5, 2010.

Costa Rican Opposition for Application No. 2011-0519; mailed Feb. 29, 2012.

COMPOUNDS

This application claims the benefit of U.S. Provisional application No. 61/166,325, filed Apr. 3, 2009, the disclosure of which is incorporated by reference herein in its entirety.

The present invention relates to compounds having glucocorticosteroid receptor agonist activity, pharmaceutical compositions containing them and their therapeutic use, particularly for the treatment of inflammatory and allergic conditions.

Glucocorticosteroids (GCs) that have anti-inflammatory properties are known and are widely used for the treatment of diseases such as inflammatory arthritides (e.g. rheumatoid arthritis, ankylosing spondylitis and psoriatic arthropathy), other rheumatoid diseases such as systemic lupus erythematosis, scleroderma, vascutitides including temporal arteritis and polyarteritis nodosa, inflammatory bowel disease such as Crohns disease and ulcerative colitis, lung diseases such as asthma and chronic obstructive airways disease, as well as many other conditions such as polymyalgia rheumatica. GCs have also been used very extensively for their immunosuppressive properties in the prevention and treatment of transplant rejection. Finally GCs have been used for their anti-tumour effects in a number of malignancies.

GCs act via specific glucocorticoid receptors (GR) that are members of the nuclear receptor superfamily. Ligand binding promotes receptor dimerisation, DNA binding, and transcriptional activation. This mechanism of GC action is well defined in vitro and is critical for regulation of the hypothalamic-pituitary-adrenal axis, gluconeogenesis as well as transcription of anti-inflammatory genes such as mitogen-activated protein kinase phosphatase-1 (MKP-1) and secretory leukocyte protease inhibitor (SLPI) in vivo. Ligand-bound receptor is also able to suppress gene transcription in a dimerisation-independent manner by interfering with the activity of transcription factors, such as AP-1 and NFkB, which are critically involved in the inflammatory reaction.

After ligand binding, the GR translocates from the cytoplasm of the cell to the nucleus and binds to glucocorticoid response elements in regulator regions of target genes. The activated GR then recruits co-factors, including the glucocorticoid receptor interacting protein 1 (GRIP-1) and steroid receptor co-activator 1 (SRC1). These accessory proteins bind to the receptor and link the GR with the general transcription machinery to drive transcription of target genes.

Glucocorticoid effects on transcription may be mediated by both the direct binding of activated GR to target DNA, homodimerisation and recruitment of co-activators (known as "transactivation") but also by GR interfering with other transcription factor function, including AP-1 and NFkB, by complexing with these other transcription factors and preventing them from binding to their target genes leading to repression of the genes normally upregulated by AP-1 or NFkB (known as "transrepression"). These two modes of receptor activity are dissociable and negative effects on NFkB activity can be retained in the absence of transactivation. It appears that transrepression is largely responsible for mediating the therapeutically desirable anti-inflammatory activity of the GR. Interestingly, the $IC_{50}$ for inhibition of AP-1 or NFkB (0.04 nM) is lower than the $EC_{50}$ for activation of is target genes (5 nM) and yet high doses of GCs are frequently required to treat patients with inflammatory disease. One explanation is that cytokines expressed at the site of inflammation may induce relative glucocorticoid resistance, for instance by activating AP-1 or NFkB. This is of importance as many pro-inflammatory cytokines signal by activation of NFkB and a major anti-inflammatory action of GCs is thought to be mediated by opposing NFkB action.

Published Japanese Patent Application No. 60067495 describes certain pregnenopyrazoles as anti-inflammatory agents.

Our co-pending International Patent Application No. PCT/GB2008/050890 relates to compounds of formula

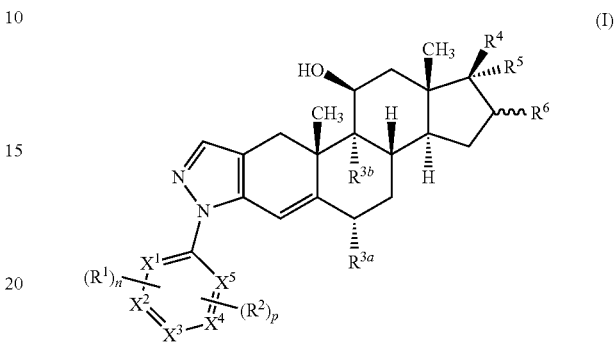

wherein
$X^1$, $X^2$, $X^3$, $X^4$ and $X^5$ each independently represent CH or a nitrogen atom, provided that no more than two of $X^1$, $X^2$, $X^3$, $X^4$ and $X^5$ may simultaneously represent a nitrogen atom;

n and p each independently represent 0 or 1;

$R^1$ represents a halogen atom or a methyl or a methoxy group;

$R^2$ represents a halogen atom, —C(O)OCH$_3$, —C(O)—S—CH$_2$CN, —C(O)—S—CH$_3$, —C(O)-heterocyclyl, —SO$_2$CH$_3$, a C$_2$-C$_6$ alkenyl group, or a methyl group optionally substituted by halogen, hydroxyl, methoxy, —OCH$_2$CH=CH$_2$ or —NR$^7$R$^8$;

$R^{3a}$ represents a hydrogen atom or methyl group and $R^{3b}$ represents a hydrogen or fluorine atom;

$R^4$ represents —C(O)—S—C(O)N(CH$_3$)$_2$, —C(O)CH$_2$Cl, —C(O)—Y—CH(R$^{11}$)—R$^9$ or —C(O)—CH(R$^{11}$)—Y—R$^9$;

$R^5$ represents hydroxyl, —OCH$_2$SCH$_3$, —O—C(O)—R$^{10}$, —O—C(O)—NH—R$^{10}$, —O—C(O)—O—R$^{10}$ or —O—C(O)—S—R$^{10}$;

$R^6$ represents a hydrogen or a halogen atom or a methyl group, and when $R^5$ is other than a hydroxyl group, $R^6$ may additionally represent a hydroxyl group;

$R^7$ and $R^8$ each independently represent a hydrogen atom, or a C$_1$-C$_3$ alkyl or a C$_1$-C$_3$ hydroxyalkyl group, or $R^7$ and $R^8$ together with the nitrogen atom to which they are attached form a 3- to 8-membered saturated or partially saturated heterocyclic ring optionally containing a further ring heterogroup selected from nitrogen, S(O)$_m$ and oxygen, the heterocyclic ring being optionally substituted by at least one substituent selected from hydroxyl, C$_1$-C$_3$ alkyl and C$_1$-C$_3$ hydroxyalkyl;

m is 0, 1 or 2;

Y represents an oxygen or sulphur atom or a group >NH;

$R^9$ represents hydrogen, halogen, cyano, —S—CN, —C(O)N(R$^{12}$)$_2$,

C$_1$-C$_6$ alkoxycarbonyl, C$_1$-C$_6$ alkylcarbonyl (optionally substituted by —OC(O)CH$_3$), C$_1$-C$_6$ alkylcarbonyloxy, C$_1$-C$_6$ alkoxy, C$_1$-C$_6$ alkylthio, —C(O)—S—C$_1$-C$_6$ alkyl, —C(=CH$_2$)—O—CH$_2$OCH$_3$, C$_1$-C$_6$ alkyl, C$_2$-C$_6$ alkenyl, C$_2$-C$_6$ alkynyl or C$_3$-C$_7$ cycloalkyl, the latter four groups being optionally substituted by one or more substituents independently selected from halogen, hydroxyl, cyano, hydroxymethyl, $C_1$-$C_4$ alkoxy and $C_1$-$C_4$ alkylcarbonyloxy;

$R^{10}$ represents $C_1$-$C_6$ alkyl (optionally substituted by halogen, $C_1$-$C_4$ alkoxy, $C_1$-$C_4$ alkylcarbonyloxy or $C_3$-$C_7$ cycloalkyl) or a 3- to 10-membered saturated or unsaturated carbocyclic or heterocyclic ring system which ring system may be optionally substituted by at least one substituent selected from halogen, carboxyl, hydroxyl, oxo, nitro, cyano, mercapto, $C_1$-$C_6$ alkyl, $C_2$-$C_6$ alkenyl, $C_1$-$C_6$ haloalkyl, $C_1$-$C_6$ hydroxyalkyl, $C_1$-$C_6$ alkoxy, $C_1$-$C_6$ haloalkoxy, $C_1$-$C_6$ alkylthio, $C_1$-$C_6$ alkylsulphinyl, $C_1$-$C_6$ alkylsulphonyl, $C_1$-$C_6$ alkylcarbonyl, $C_1$-$C_6$ alkylcarbonyloxy, $C_1$-$C_6$ alkoxycarbonyl, amino (—$NH_2$), carboxamido (—$CONH_2$), (mono) $C_1$-$C_6$ alkylamino, (di) $C_1$-$C_6$ alkylamino and phenyl;

$R^{11}$ represents a hydrogen atom or a methyl group; and each $R^{12}$ independently represents a hydrogen atom or a methyl group; provided that when $R^4$ represents —C(O)CH$_2$OH, —C(O)CH$_2$OC(O)C$_2$H$_5$ or —C(O)CH$_2$Cl, $X^1$, $X^2$, $X^3$, $X^4$ and $X^5$ each represent CH and $R^5$ represents —O—C(O)—$R^{10}$ where $R^{10}$ represents $C_1$-$C_6$ alkyl, then at least one of $R^1$ and $R^2$ is present;

or a pharmaceutically acceptable salt thereof.

The present invention provides compounds falling within the scope of formula (I) of, but not specifically disclosed in, our co-pending International Patent Application No. PCT/GB2008/050890 referred to above.

Thus, the present invention provides a compound of formula (I) as hereinbefore defined selected from the group consisting of:

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-1-{[(Cyanomethyl)sulfanyl]carbonyl}-10b-fluoro-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate, (1R,3aS,3bS,10aS,10bR,11S,12aS)-10b-Fluoro-7-(6-fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7, 10,10a,10b,11,12,12a-tetradecahydrocyclopenta[5,6]naphtho[1,2-f]indazol-1-yl(2S)-tetrahydrofuran-2-carboxylate, (1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a, 10b,11,12,12a-tetradecahydrocyclopenta[5,6]naphtho[1,2-f]indazol-1-yl (S)/(R) tetrahydrofuran-2-carboxylate, (1R,3aS,3bS,10aS,10bR,11S,12aS)-1-{[Cyanomethyloxy]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[Cyanomethyloxy]carbonyl}-7-(6-fluoropyridin-3-yl)-11-hydroxy-10a,12a-dimethyl-1,2,3,3a,3b,4,5,7, 10,10a,10b,11,12,12a-tetradecahydrocyclopenta[5,6]naphtho[1,2-f]indazol-1-yl cyclopropanecarboxylate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10 10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10, 10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3 a,3b,4,5,7,10, 10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10, 10a,10b,11,12,12a-tetradecahydrocyclopenta[5,6]naphtho[1,2-f]indazol-1-yl 1,3-oxazole-4-carboxylate, and (1R,2R,3aS,3bS,10aS,10bR,11S,12aS)-10b-Fluoro-1-{[(cyanomethyl)sulfanyl]carbonyl}-7-(6-fluoropyridin-3-yl)-11-hydroxy-2,10a,12a-trimethyl-1,2,3,3a,3b,4,5,7,10, 10a,10b,11,12,12a-tetradecahydrocyclopenta[5,6]naphtho[1,2-f]indazol-1-yl methoxyacetate, or a pharmaceutically acceptable salt of any one thereof.

It should be noted that each of the chemical compounds listed above represents a particular and independent aspect of the invention.

The compounds of formula (I) referred to above and those of the present invention may form pharmaceutically acceptable salts, e.g., an acid addition salt such as a hydrochloride, hydrobromide, trifluoroacetate, sulphate, phosphate, acetate, fumarate, maleate, tartrate, lactate, citrate, pyruvate, succinate, oxalate, methanesulphonate or p-toluenesulphonate salt.

It will be understood that the compounds of the present invention and pharmaceutically acceptable salts thereof may exist in solvated, for example hydrated, as well as unsolvated forms, and the present invention encompasses all such solvated forms. Tautomers and mixtures thereof also form an aspect of the present invention.

The compounds of the present invention and their pharmaceutically acceptable salts have activity as pharmaceuticals, in particular as modulators of glucocorticoid receptor activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis;cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;
4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
5. allograft rejection: acute and chronic following, for example, transplantation of kidney, heart, liver, lung, bone marrow, skin or cornea or following blood transfusion; or is chronic graft versus host disease;
6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, para-influenza; bacterial diseases such as tuberculosis and mycobacterium avium, leprosy; other infectious diseases, such as fungal diseases, chlamydia, candida, aspergillus, cryptococcal meningitis, pneumocystis carni, cryptosporidiosis, histoplasmosis, toxoplasmosis, trypanosome infection and leishmaniasis.

Thus, the present invention provides a compound of formula (I) as hereinbefore defined selected from the group consisting of:

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-1-{[(Cyanomethyl)sulfanyl]carbonyl}-10b-fluoro-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[1,2-f]indazol-1-yl(2R)-tetrahydrofuran-2-carboxylate, (1R,3aS,3bS,10aS,10bR,11S,12aS)-10b-Fluoro-7-(6-fluoropyridin-3-yl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(R)/(S) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(S)/(R) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b, 4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b, 4,5,7,10,10a,10b,11,12,12a-tetradecahydrocyclopenta[5,6]naphtho[1,2-f]indazol-1-yl (R)/(S)tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b, 4,5,7,10,10a,10b,11,12,12a-tetradecahydrocyclopenta[5,6]naphtho[1,2-f]indazol-1-yl (S)/(R) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7, 10,10a,10b,11,12,12a-tetradecahydrocyclopenta[5,6]naphtho[1,2-f]indazol-1-yl(2S)-tetrahydrofuran-2-carboxylate, (1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a, 10b,11,12,12a-tetradecahydrocyclopenta[5,6]naphtho[1,2-f]indazol-1-yl (S)/(R) tetrahydrofuran-2-carboxylate, (1R,3aS,3bS,10aS,10bR,11S,12aS)-1-{[Cyanomethyloxy]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[Cyanomethyloxy]carbonyl}-7-(6-fluoropyridin-3-yl)-11-hydroxy-10a,12a-dimethyl-1,2,3,3a,3b,4,5,7, 10,10a,10b,11,12,12a-tetradecahydrocyclopenta[5,6]naphtho[1,2-f]indazol-1-yl cyclopropanecarboxylate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, and (1R,2R,3aS,3bS,10aS,10bR,11S,12aS)-10b-Fluoro-1-{[(cyanomethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, or a pharmaceutically acceptable salt thereof for use in therapy.

In a further aspect, the present invention provides the use of a compound of formula (I) as hereinbefore defined selected from the group consisting of:

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7, 10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7, 10,10a,10b,11,12,12a-tetradecahydrocyclopenta[5,6]naphtho[1,2-f]indazol-1-yl propanoate, (1R,2R,3aS,3bS,10aS,10bR,11S,12aS)-1-{[(Cyanomethyl)sulfanyl]carbonyl}-10b-fluoro-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7, 10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10, 10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5, 7,10,10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-10b-Fluoro-7-(6-fluoropyridin-3-yl)-11-hydroxy-1-{[(2-hydroxyethyl)sulfanyl]carbonyl}-10a,12a-dimethyl-1,2,3,3a,3b,4,5, 7, 10, 10a, 10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5, 7,10,10a,10b,11,12,12a-tetradecahydrocyclopenta[5,6]naphtho[1,2-f]indazol-1-yl(R)/(S) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(S)/(R) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(2S)-tetrahydrofuran-2-carboxylate, (1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-2-carboxylate, (1R,3aS,3bS,10aS,10bR,11S,12aS)-1-{[Cyanomethyloxy]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[Cyanomethyloxy]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, and (1R,2R,3aS,3bS,10aS,10bR,11S,12aS)-10b-Fluoro-1-{[(cyanomethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, or a pharmaceutically acceptable salt thereof, in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the present invention (including pharmaceutically acceptable salts) may be used in the treatment of asthma {such as bronchial, allergic, intrinsic, extrinsic or dust asthma, particularly chronic or inveterate asthma (for example late asthma or airways hyper-responsiveness)}, chronic obstructive pulmonary disease (COPD) or allergic rhinitis.

The invention also provides a method of treating, or reducing the risk of, an obstructive airways disease or condition (e.g. asthma or COPD) which comprises administering to a patient in need thereof a therapeutically effective amount of a compound of formula (I) as hereinbefore defined selected from the group consisting of:

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-1-{[(Cyanomethyl)sulfanyl]carbonyl}-10b-fluoro-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5, 7,10,10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-10b-Fluoro-7-(6-fluoropyridin-3-yl)-11-hydroxy-1-{[(2-hydroxyethyl)sulfanyl]carbonyl}-10a,12a-dimethyl-1,2,3,3a,3b,4,5, 7, 10, 10a, 10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5, 7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5, 7,10,10a,10b,11,12,12a-tetradecahydrocyclopenta[5,6]naphtho[1,2-f]indazol-1-yl(R)/(S) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(S)/(R) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(2S)-tetrahydrofuran-2-carboxylate, (1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-2-carboxylate, (1R,3aS,3bS,10aS,10bR,11S,12aS)-1-{[Cyanomethyloxy]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[Cyanomethyloxy]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, and (1R,2R,3aS,3bS,10aS,10bR,11S,12aS)-10b-Fluoro-1-{[(cyanomethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, or a pharmaceutically acceptable salt thereof.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of the invention and pharmaceutically acceptable salts thereof may be used on their own but will generally be administered in the form of a pharmaceutical composition in which the compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I) as hereinbefore defined selected from the group consisting of:

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-1-{[(Cyanomethyl)sulfanyl]carbonyl}-10b-fluoro-7-(6-fluoropyridin-3-yl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10, 10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-10b-Fluoro-7-(6-fluoropyridin-3-yl)-11-hydroxy-1-{[(2-hydroxyethyl)sulfanyl]carbonyl}-10a,12a-dimethyl-1,2,3,3a,3b,4,5, 7, 10, 10a,10b,11,12,12a-tetradecahydrocyclopenta[5,6]naphtho[1,2-f]indazol-1-yl(2R)-tetrahydrofuran-2-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(R)/(S) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(S)/(R) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate, (1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate, (1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl(2S)-tetrahydrofuran-2-carboxylate, (1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-2-carboxylate, (1R,3aS,3bS,10aS,10bR,11S,12aS)-1-{[Cyanomethyloxy]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,10aS,10bR,11S,12aS)-1-{[Cyanomethyloxy]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl furan-2-carboxylate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3 a,3b,4,5,7,10,10a,10b,11,12,12a-tetradecahydrocyclopenta[5,6]naphtho[1,2-f]indazol-1-yl cyclopropanecarboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl propanoate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl methoxyacetate, (1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, (1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3 a,3b,4,5,7,10,10a,10b,11,12,12a-tetradecahydrocyclopenta[5,6]naphtho[1,2-f]indazol-1-yl 1,3-oxazole-4-carboxylate, and (1R,2R,3aS,3bS,10aS,10bR,11S,12aS)-10b-Fluoro-1-{[(cyanomethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate, or a pharmaceutically acceptable salt thereof, in association with a pharmaceutically acceptable adjuvant, diluent or carrier.

The invention further provides a process for the preparation of a pharmaceutical composition of the invention which comprises mixing a compound of the invention or a pharmaceutically acceptable salt thereof with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the invention and pharmaceutically acceptable salts thereof may be administered by oral or nasal inhalation. For inhalation, the compound/salt is desirably finely divided. The finely divided compound/salt preferably has a mass median diameter of less than 10 micrometres (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention and pharmaceutically acceptable salts thereof may also be administered by means of a dry powder inhaler. The inhaler may be a single or a multi dose inhaler, and may be a breath actuated dry powder inhaler.

One possibility is to mix the finely divided compound/salt with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound/salt may be coated by another substance. The powder mixture may also be dispensed into hard gelatine capsules, each containing the desired dose of the active ingredient.

Another possibility is to process the finely divided powder into spheres that break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention (or pharmaceutically acceptable salt thereof) may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention (or pharmaceutically acceptable salt thereof) may be admixed with, for example, a vegetable oil or polyethylene glycol. Hard gelatine capsules may contain granules of the compound/salt using the above-mentioned excipients for tablets. Also liquid or semi-solid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention and pharmaceutically acceptable salts thereof may also be administered in conjunction with other compounds used for the treatment of the above conditions.

The invention therefore further relates to combination therapies wherein a compound of the invention or a pharmaceutically acceptable salt thereof, or a pharmaceutical composition or formulation comprising a compound of the invention or a pharmaceutically acceptable salt thereof, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention and their pharmaceutically acceptable salts may be combined with the following agents: non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention or a pharmaceutically acceptable salt thereof together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention or a pharmaceutically acceptable salt thereof with a monoclonal antibody targeting B-Lymphocytes (such as CD20 (rituximab), MRA-aIL16R and T-Lymphocytes, CTLA4-Ig, HuMax 11-15).

The present invention still further relates to the combination of a compound of the invention or a pharmaceutically acceptable salt thereof with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention or a pharmaceutically acceptable salt thereof with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention or a pharmaceutically acceptable salt thereof and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention or a pharmaceutically acceptable salt thereof and a receptor antagonist for leukotrienes (LT) B4, LTC4, LTD4, and LTE4 selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention or a pharmaceutically acceptable salt thereof and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention or a pharmaceutically acceptable salt thereof and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention or a pharmaceutically acceptable salt thereof and a proton pump inhibitor (such as omeprazole) or a gastroprotective histamine type 2 receptor antagonist.

The present invention further relates to the combination of a compound of the invention or a pharmaceutically acceptable salt thereof and an antagonist of the histamine type 4 receptor.

The present invention still further relates to the combination of a compound of the invention or a pharmaceutically acceptable salt thereof and an alpha-1/alpha-2 adrenoreceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention or a pharmaceutically acceptable salt thereof and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention or a pharmaceutically acceptable salt thereof and a beta-adrenoreceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention or a pharmaceutically acceptable salt thereof and a chromone, such as sodium cromoglycate or nedocromil sodium.

The present invention further relates to the combination of a compound of the invention or a pharmaceutically acceptable salt thereof with an agent that modulates a nuclear hormone receptor such as PPARs.

The present invention still further relates to the combination of a compound of the invention or a pharmaceutically acceptable salt thereof together with an immunoglobulin (Ig) or Ig preparation or an antagonist or antibody modulating Ig function such as anti-IgE (for example omalizumab).

The present invention further relates to the combination of a compound of the invention or a pharmaceutically acceptable salt thereof and another systemic or topically-applied anti-inflammatory agent, such as thalidomide or a derivative thereof, a retinoid, dithranol or calcipotriol.

The present invention still further relates to the combination of a compound of the invention or a pharmaceutically acceptable salt thereof and combinations of aminosalicylates and sulfapyridine such as sulfasalazine, mesalazine, balsalazide, and olsalazine; and immunomodulatory agents such as the thiopurines.

The present invention further relates to the combination of a compound of the invention or a pharmaceutically acceptable salt thereof together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention or a pharmaceutically acceptable salt thereof and a cardiovascular agent such as a calcium channel blocker, a beta-adrenoreceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention or a pharmaceutically acceptable salt thereof and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention or a pharmaceutically acceptable salt thereof and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention or a pharmaceutically acceptable salt thereof together with a parenterally or topically-applied (including inhaled) local anaesthetic agent such as lignocaine or a derivative thereof.

A compound of the invention or a pharmaceutically acceptable salt thereof can also be used in combination with an anti-osteoporosis agent including a hormonal agent such as raloxifene, or a biphosphonate such as alendronate.

The present invention still further relates to the combination of a compound of the invention or a pharmaceutically acceptable salt thereof together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant to receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; (xxvii) inhibitor of transcription factor activation such as NFkB, API, or STATS; or (xxviii) a glucocorticoid receptor agonist.

In a further aspect the present invention provides a (fixed dose) combination (for example for the treatment of COPD, asthma or allergic rhinitis) of a compound of the invention or a pharmaceutically acceptable salt thereof as hereinbefore defined, one or more agents independently selected from:
  a selective $\beta_2$ adrenoreceptor agonist (such as metaproterenol, isoproterenol, isoprenaline, albuterol, salbutamol, formoterol, salmeterol, terbutaline, orciprenaline, bitolterol mesylate, pirbuterol or indacaterol);
  a phosphodiesterase inhibitor (such as a PDE4 inhibitor);
  a protease inhibitor (such as a neutrophil elastase or matrix metalloprotease MMP-12 inhibitor);
  an anticholinergic agent;
  a modulator of chemokine receptor function (such as a CCR1 receptor antagonist); and
  an inhibitor of kinase function (such as the kinases p38 or IKK); and optionally one or more pharmaceutically acceptable excipients.

The invention also provides a pharmaceutical product comprising a preparation of a first active ingredient which is a compound of the invention or a pharmaceutically acceptable salt thereof as hereinbefore defined, and a preparation of a second active ingredient which is:
  a selective $\beta_2$ adrenoreceptor agonist;
  a phosphodiesterase inhibitor;
  a protease inhibitor;
  an anticholinergic agent;
  a modulator of chemokine receptor function; or
  an inhibitor of kinase function;
wherein the preparations are for simultaneous, sequential or separate administration to a patient in need thereof.

In another aspect, the invention provides a kit comprising a preparation of a first active ingredient which is a compound of the invention or a pharmaceutically acceptable salt thereof as hereinbefore defined, and a preparation of a second active ingredient which is:
  a selective $\beta_2$ adrenoreceptor agonist;
  a phosphodiesterase inhibitor;
  a protease inhibitor;
  an anticholinergic agent;
  a modulator of chemokine receptor function; or
  an inhibitor of kinase function;
and instructions for the simultaneous, sequential or separate administration of the preparations to a patient in need thereof.

A compound of the invention or a pharmaceutically acceptable salt thereof can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, ici raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of is 5α-reductase such as finasteride;
(iii) an agent which inhibits cancer cell invasion (for example a metalloproteinase inhibitor like marimastat or an inhibitor of urokinase plasminogen activator receptor function);
(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin av133 function or an angiostatin);
(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The present invention will now be further explained by reference to the following illustrative examples in which the following abbreviations are used:

EtOAc ethyl acetate
HCl hydrochloric acid
$H_2S$ hydrogen sulphide
$CH_2Cl_2$ dichloromethane (DCM)
DMF N,N-dimethylformamide
NaH sodium hydride
$MgSO_4$ magnesium sulphate
$NaNO_2$ sodium nitrite
$K_2CO_3$ potassium carbonate
$SnCl_2$ tin (II) chloride
NaOH sodium hydroxide
$Na_2SO_4$ sodium sulphate
$NH_4Cl$ ammonium chloride
DIEA diisopropylethylamine
DME dimethyl ether
DCM dichloromethane
DMSO dimethylsulfoxide
EtOH ethanol
$Et_2O$ diethyl ether
THF tetrahydrofuran
TFA trifluoroacetic acid
HCl hydrochloric acid
$NaHCO_3$ sodium hydrogen carbonate
$Et_3N$ triethylamine
MeOH methanol
MeCN/ acetonitrile
$CH_3CN$
EDTA ethylenediaminetetraacetic acid
NMP N-methylpyrrolidine
conc. concentrated
rt room temperature
h hours
min minutes
M molar
MS mass spectrometry
APCI atmospheric chemical ionisation method
ESI electron spray ionisation method
NMR nuclear magnetic resonance
SCX solid phase extraction with a sulfonic acid sorbent
HPLC high performance liquid chromatography
LC-MS liquid chromatography with mass spectrometry detection General Methods NMR spectra were recorded on a Varian Mercury-VX 300 MHz instrument or a Varian Inova 400 MHz instrument. The central peaks of chloroform-d (H 7.26 ppm), acetone-$d_6$ (H 2.05 ppm), acetonitrile-$d_3$ ($\delta_H$ 1.94 ppm) or DMSO-$d_6$ (H 2.50 ppm) were used as internal references.

The following method was used for LC/MS analysis:
Instrument Agilent 1100; Column Waters Symmetry 2.1×30 mm; Mass APCI; Flow rate 0.7 mL/min; Wavelength 254 nm; Solvent A: water+0.1% TFA; Solvent B: acetonitrile+0.1% TFA; Gradient 15-95%/B 2.7 min, 95% B 0.3 min.

Column chromatography was carried out using silica gel (0.040-0.063 mm, Merck). For preparative HPLC either a Kromasil® KR-100-5-C18 column (250×20 mm, Akzo Nobel) and mixtures of acetonitrile/water (0.1% TFA) at a flow rate of 10 ml/min or a XTerra® Prep MS $C_{18}$ OBD™ Column, 5 μm, 19×50 mm (acetonitrile/water/0.1% $NH_3$) at a flow rate of 20 ml/min was used. UV=254 nm or 220 nm was used for detection.

Unless stated otherwise, starting materials were commercially available. All solvents and commercial reagents were of laboratory grade and were used as received.

Intermediate 1

(8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-1H-cyclopenta[a]phenanthren-3(2H)-one

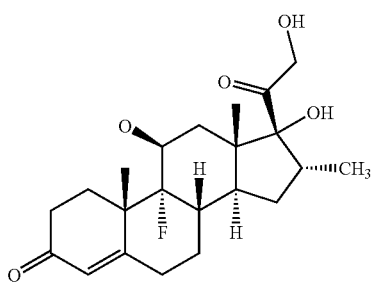

In a 1000 mL round-bottomed flask was suspended dexamethasone (10 g, 25.48 mmol) in EtOAc (400 mL) and ethanol (100 mL) and tris(triphenylphosphine)rhodium(I) chloride (Wilkinson's catalyst, 2.5 g, 2.70 mmol) was added together with a magnetic stirrer bar. The mixture was vigorously stirred in a hydrogen atmosphere (1 atm) at room temperature for 1 week and another 1.0 g of the catalyst was added. The reaction was allowed to proceed for another week and the resulting mixture was concentrated in vacuo to obtain a solid that was suspended in DCM (100 ml) and the suspension was filtered. The obtained solid was washed with 3 portions of DCM (50 ml) and dried on the sinter in air, yielding 9.6 g of the target compound as an off white solid. APCI-MS m/z: 395 [MH$^+$].

Intermediate 2

(8S,9R,10S,11S,13S,14S,16R,17R)-9-Fluoro-11,17-dihydroxy-10,13,16-trimethyl-3-oxo-2,3,6,7,8,9,10,11,12,13,14,15,16,17-tetradecahydro-1H-cyclopenta[a]phenanthrene-17-carboxylic acid

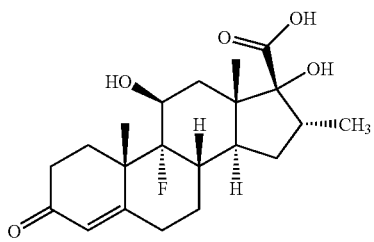

In a 500 mL round-bottomed flask was dissolved intermediate 1 (9.5 g, 24.08 mmol) in THF (200 mL) and a solution of orthoperiodic acid (10.98 g, 48.17 mmol) in 80 ml of water was added at room temperature. The obtained mixture was stirred for 2 hours at the same temperature, the organic solvent was removed in vacuo, and the resulting wet slurry was diluted with water (100 ml). The obtained solid was filtered, washed with water on the filter and dried on the sinter in a stream of air, giving 9.0 g of the desired product as an off-white solid. APCI-MS m/z: 381 [MH$^+$].

Intermediate 3

(8S,9R,10S,11S,13S,14S,16R,17R,Z)-9-Fluoro-11,17-dihydroxy-2-(hydroxymethylene)-10,13,16-trimethyl-3-oxo-2,3,6,7,8,9,10,11,12,13,14,15,16,17-tetradecahydro-1H-cyclopenta[a]phenanthrene-17-carboxylic acid

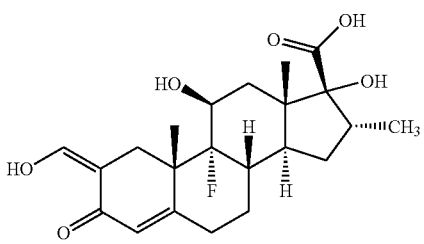

In a 1000 mL round-bottomed flask, equipped with a magnetic stirrer bar and a reflux condenser was added sodium hydride (60% in mineral oil, 10.32 g, 236.56 mmol) and dry THF (150 mL) to give a white suspension that was stirred in an atmosphere of argon at room temperature. Intermediate 2 (9 g, 23.66 mmol) was added followed by ethyl formate (96 mL, 1182.81 mmol) and the resulting mixture was stirred at the same temperature for approximately 2 hours. The reaction was quenched by careful addition of 2M NaOH (50 ml), the resulting mixture was stirred for 5 minutes and subsequently transferred to a separation funnel where the phases were allowed to separate. The aqueous phase was collected, and the organic phase was extracted with an additional 40 ml of 2M NaOH. The combined aqueous phases were diluted with water (50 ml), washed with Et$_2$O (50 ml) and acidified with 4M HCl (90 ml). The product was extracted with EtOAc (2×150 ml), and the combined organic phases were washed with brine (100 ml) and dried over Na$_2$SO$_4$. Filtration and evaporation of the organic solution in vacuo yielded 7.2 g of the desired product as an orange foam that was used in the next step without any further purification. APCI-MS m/z: 409 [MH$^+$].

Intermediate 4

(1R,2R,3aS,3bS,10aS,10bR,11S,12aS)-10b-Fluoro-7-(6-fluoropyridin-3-yl)-1,11-dihydroxy-2,10a,12a-trimethyl-1,2,3,3a,3b,4,5,7,10,10a,10b,11,12,12a-tetradecahydrocyclopenta[5,6]naphtho[1,2-f]indazole-1-carboxylic acid

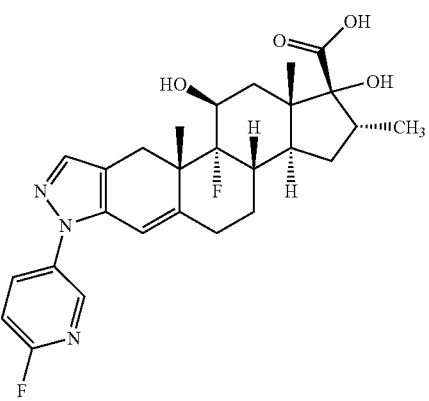

In a 500 mL round-bottomed flask was dissolved intermediate 3 (7.2 g, 17.63 mmol) in acetic acid (100 mL) and the solution was degassed with nitrogen gas, N₂. 2-Fluoro-5-hydrazinylpyridine (2.465 g, 19.39 mmol) was added at room temperature and the mixture was stirred with a magnetic stirrer for 30 minutes. The solution was freeze-dried overnight to yield 8.7 g of the desired product as an orange solid. APCI-MS m/z: 500 [MH⁺].

Intermediate 5

(1R,2R,3aS,3bS,10aS,10bR,11S,12aS)-10b-Fluoro-7-(6-fluoropyridin-3-yl)-1,11-dihydroxy-2,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid

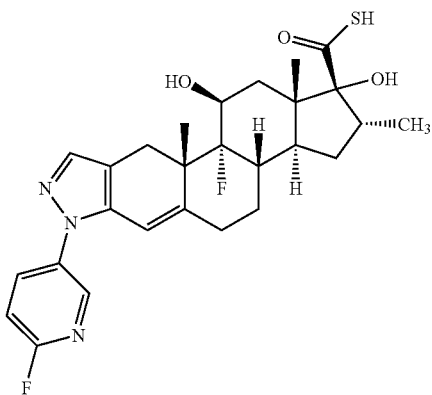

In a 100 mL round-bottomed flask was dissolved intermediate 4 (8.7 g, 17.62 mmol) in DMF (20 mL) and di(1H-imidazol-1-yl)methanone (CDI, 5.71 g, 35.23 mmol) was added at room temperature. After the gas evolution had ceased, the mixture was stirred in a sealed flask overnight. Hydrogen sulfide (H₂S) was subsequently bubbled through the solution for 10 minutes and the resulting solution was allowed to stir for another 10 minutes. The solution was added to 200 ml 1M HCl in a separation funnel and the mixture was extracted with EtOAc (2×150 ml). The combined organic phases were washed with 0.5M HCl (3×100 ml) and brine (40 ml), were subsequently dried over Na₂SO₄, filtered and the organic solvent was evaporated in vacuo to give 9.0 g of the desired product as an orange foam which was used in the next step without any further purification. APCI-MS m/z: 516 [MH⁺].

Intermediate 6

(1R,2R,3aS,3bS,10aS,10bR,11S,12aS)-10b-Fluoro-7-(6-fluoropyridin-3-yl)-11-hydroxy-2,10a,12a-trimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid

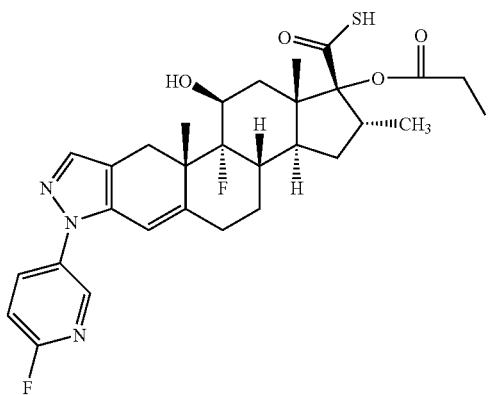

In a 50 mL round-bottomed flask was dissolved intermediate 5 (0.1 g, 0.19 mmol) and triethylamine (0.067 mL, 0.48 mmol) in DCM (10 mL) and propionyl chloride (0.038 g, 0.41 mmol) was added at room temperature. Stirring was continued for 10 minutes. N₁-ethyl-N₂,N₂-dimethylethane-1,2-diamine (0.091 mL, 0.58 mmol) was added and the mixture was stirred for another 10 minutes at the same temperature. The reaction mixture was diluted with DCM to a total volume of 25 ml and the obtained mixture was washed with 1M HCl (2×20 ml) and brine (10 ml). The organic phase was dried over Na₂SO₄, the drying agent was filtered off and the organic solvent was evaporated in vacuo to give 99 mg of the desired compound as a yellow semi-solid. APCI-MS m/z: 572 [MH⁺].

Intermediate 7

(1R,2R,3aS,3bS,10aS,10bR,11S,12aS)-10b-Fluoro-7-(6-fluoropyridin-3-yl)-11-hydroxy-2,10a,12a-trimethyl-1-[(1,3-oxazol-4-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid

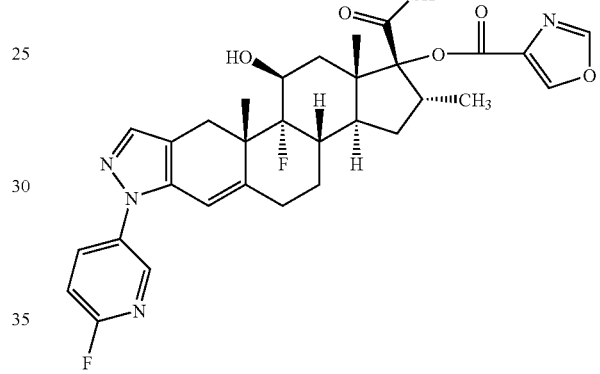

The compound was prepared according to the description for intermediate 6, starting from intermediate 5. APCI-MS m/z: 611 [MH⁺].

Intermediate 8

(1R,2R,3aS,3bS,10aS,10bR,11S,12aS)-10b-Fluoro-7-(4-fluorophenyl)-1,11-dihydroxy-2,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid

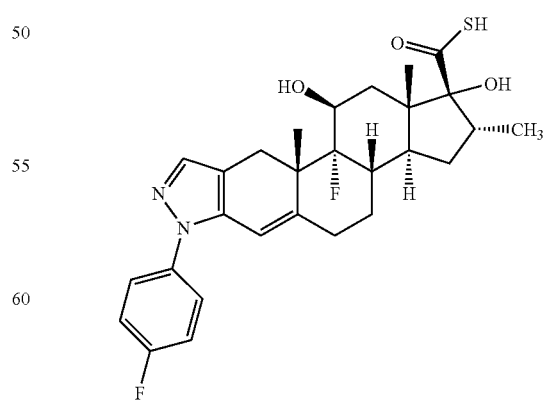

The compound was prepared according to the same procedure as described for intermediate 5. APCI-MS m/z: 515 [MH⁺].

Intermediate 9

(6S,8S,9S,10R,11S,13S,14S,17R)-11,17-Dihydroxy-17-(2-hydroxyacetyl)-6,10,13-trimethyl-6,7,8,9,10,11,12,13,14,15,16,17-dodecahydro-1H-cyclopenta[a]phenanthren-3(2H)-one

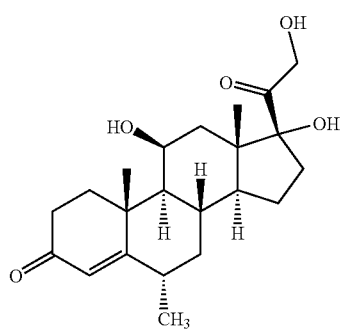

In a 250 mL round-bottomed flask was suspended (6S,8S,9S,10R,11S,13S,14S,17R)-11,17-dihydroxy-17-(2-hydroxyacetyl)-6,10,13-trimethyl-6,7,8,9,10,11,12,13,14,15,16,17-dodecahydro-3H-cyclopenta[a]phenanthren-3-one (6α-Methylprednisolon, 4.3 g, 11.48 mmol) in EtOAc (80 mL) and the reaction mixture was diluted with ethanol (20.0 mL). Tris(triphenylphosphine)rhodium(I)chloride (Wilkinson's catalyst, 1 g, 1.08 mmol) was added together with a magnetic stirrer bar and the flask was vigorously stirred in a hydrogen atmosphere (1 atm) at room temperature for 1 week. The reaction mixture was filtered through a glass filter funnel and the filtrate was concentrated in vacuo to yield 4.07 g of the desired compound as a light brown solid which was used in the next step without any further purification. APCI-MS m/z: 377 [MH$^+$].

Intermediate 10

(6S,8S,9S,10R,11S,13S,14S,17R)-11,17-Dihydroxy-6,10,13-trimethyl-3-oxo-2,3,6,7,8,9,10,11,12,13,14,15,16,17-tetradecahydro-1H-cyclopenta[a]phenanthrene-17-carboxylic acid

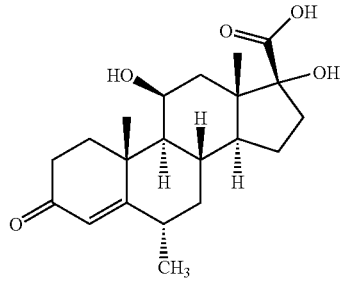

The compound was prepared according to the procedure described for intermediate 2, starting from intermediate 9. APCI-MS m/z: 363 [MH$^+$].

Intermediate 11

(6S,8S,9S,10R,11S,13S,14S,17R,Z)-11,17-Dihydroxy-2-(hydroxymethylene)-6,10,13-trimethyl-3-oxo-2,3,6,7,8,9,10,11,12,13,14,15,16,17-tetradecahydro-1H-cyclopenta[a]phenanthrene-17-carboxylic acid

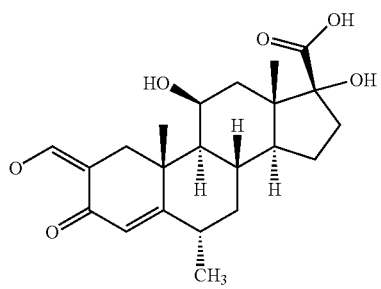

The compound was prepared according to the description for intermediate 3, starting from intermediate 10. APCI-MS m/z: 391 [MH$^+$].

Intermediate 12

(1R,3aS,3bS,5S,10aR,10bS,11S,12aS)-7-(6-Fluoropyridin-3-yl)-1,11-dihydroxy-5,10a,12a-trimethyl-1,2,3,3a,3b,4,5,7,10,10a,10b,11,12,12a-tetradecahydrocyclopenta[5,6]naphtho[1,2-f]indazole-1-carboxylic acid

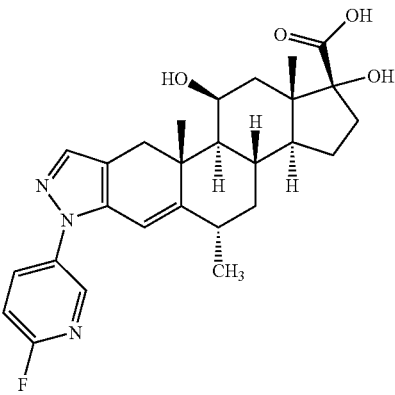

The compound was prepared according to the procedure described for intermediate 4, starting from intermediate 11. APCI-MS m/z: 482 [MH$^+$].

Intermediate 13

(1R,3aS,3bS,5S,10aR,10bS,11S,12aS)-7-(6-Fluoro-pyridin-3-yl)-1,11-dihydroxy-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid

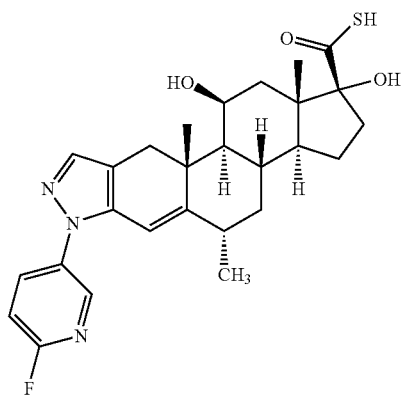

The compound was prepared according to the description for intermediate 5, starting from intermediate 12. APCI-MS m/z: 498 [MH$^+$].

Intermediate 14

(1R,3aS,3bS,5S,10aR,10bS,11S,12aS)-7-(6-Fluoro-pyridin-3-yl)-11-hydroxy-5,10a,12a-trimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid

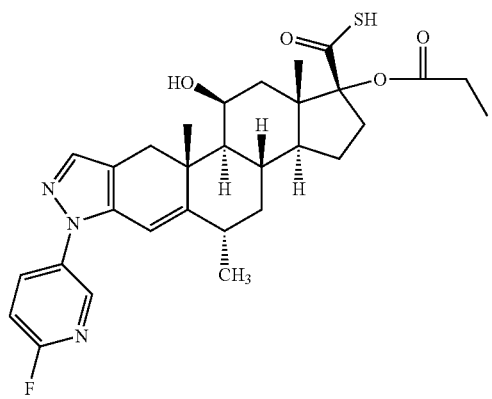

The compound was prepared according to the description for intermediate 6, starting from intermediate 13. APCI-MS m/z: 554 [MH$^+$].

Intermediate 15

(1R,3aS,3bS,5S,10aR,10bS,11S,12aS)-7-(6-Fluoro-pyridin-3-yl)-11-hydroxy-1-[(methoxyacetyl)oxy]-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid

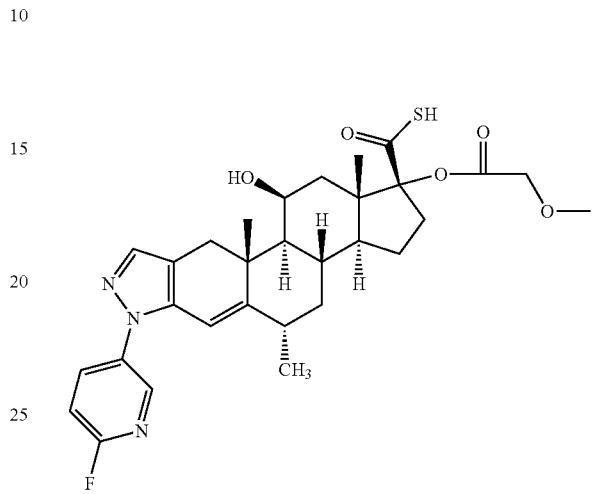

The compound was prepared according to the description for intermediate 6, starting from intermediate 13. APCI-MS m/z: 570 [MH$^+$].

Intermediate 16

(1R,3aS,3bS,5S,10aR,10bS,11S,12aS)-7-(6-Fluoro-pyridin-3-yl)-11-hydroxy-5,10a,12a-trimethyl-1-[(1,3-oxazol-4-ylcarbonyl)oxy]-1,2,3,3a,3b,4,5,7,10,10a,10b,11,12,12a-tetradecahydrocyclopenta[5,6]naphtho[1,2f]indazole-1-carbothioic S-acid

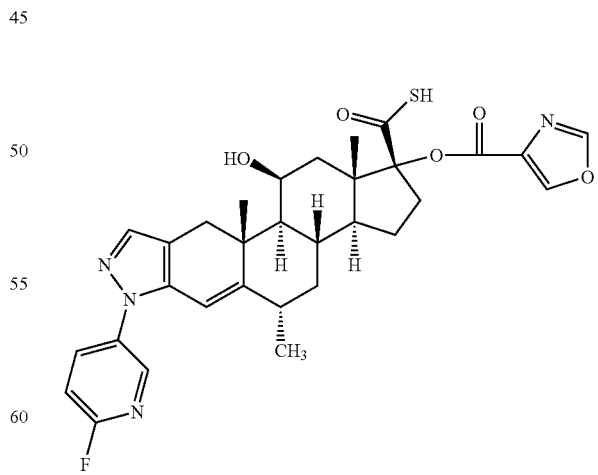

The compound was prepared according to the description for intermediate 6, starting from intermediate 13. APCI-MS m/z: 593 [MH$^+$].

Intermediate 17

(1R,3aS,3bS,5S,10aR,10bS,11S,12aS)-1-[(Cyclopropylcarbonyl)oxy]-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid

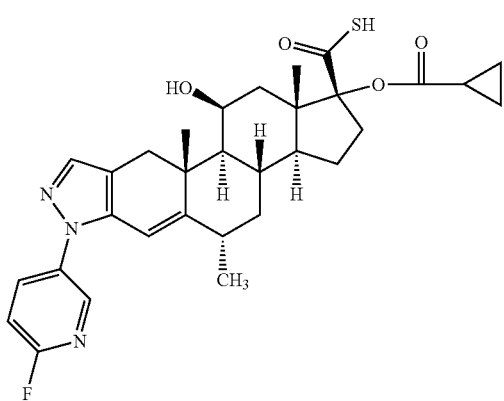

The compound was prepared according to the description for intermediate 6, starting from intermediate 13. APCI-MS m/z: 566 [MH+].

Intermediate 18

(8S,9R,10S,11S,13S,14S,17R)-9-Fluoro-11,17-dihydroxy-10,13-dimethyl-3-oxo-2,3,6,7,8,9,10,11,12,13,14,15,16,17-tetradecahydro-1H-cyclopenta[a]phenanthrene-17-carboxylic acid

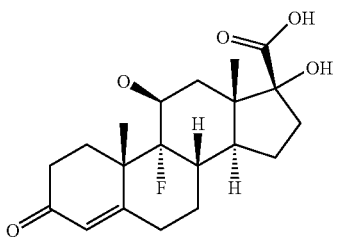

In a 1000 mL round-bottomed flask was suspended 2-((8S,9R,10S,11S,13S,14S,17R)-9-fluoro-11,17-dihydroxy-10,13-dimethyl-3-oxo-2,3,6,7,8,9,10,11,12,13,14,15,16,17-tetradecahydro-1H-cyclopenta[a]phenanthren-17-yl)-2-oxoethyl acetate (Fludrocortisone-21-acetate, 22.8 g, 53.97 mmol) in MeOH (200 mL) and the suspension was degassed with nitrogen. 2M sodium hydroxide (40.5 mL, 80.95 mmol) was added to the solution and the mixture was stirred for 10 minutes. To the solution was added 4M HCl (20 ml, 80 mmol) and MeOH was removed in vacuo. The obtained residue was dissolved in THF (200 ml), a solution of orthoperiodic acid (15.99 g, 70.16 mmol) in water (40 ml) was added at room temperature and the obtained mixture was stirred for 1 hour. 100 ml of water was added and the organic solvent was removed in vacuo. An additional 100 ml of water was added to the aqueous residue and the obtained solid was collected by filtration, was washed with water (2×200 ml) and was air dried on the sinter, followed by drying in vacuo to yield 20 g of the desired compound as an off-white solid. APCI-MS m/z: 367 [MH+].

Intermediate 19

(8S,9R,10S,11S,13S,14S,17R,Z)-9-Fluoro-11,17-dihydroxy-2-(hydroxymethylene)-10,13-dimethyl-3-oxo-2,3,6,7,8,9,10,11,12,13,14,15,16,17-tetradecahydro-1H-cyclopenta[a]phenanthrene-17-carboxylic acid

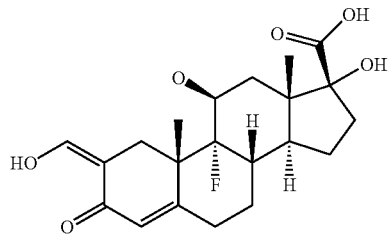

To a stirred suspension of sodium hydride (6.55 g, 272.91 mmol) (10.9 g, 60% suspension in mineral oil) in THF (130 mL) was added intermediate 18 (10 g, 27.29 mmol) in 2-3 portions followed by ethyl formate (111 mL, 1364.54 mmol). The mixture was stirred at room temperature for approximately 2 hours in an argon atmosphere. The reaction was quenched by careful addition of 2M NaOH (50 ml) and the phases were separated. The organic phase was extracted with an additional 2×20 ml of 2M NaOH. The combined aqueous solutions were diluted with water (15 ml), washed with Et₂O (40 ml) and acidified by addition of 4M HCl. The product was extracted with EtOAc (3×100 ml) and the combined organic phases were washed with brine (30 ml), dried over Na₂SO₄, filtered and evaporated in vacuo to give 8.6 g of the desired product as an orange semi-solid which was used directly in the next step without any further purification. APCI-MS m/z: 395 [MH+].

Intermediate 20

(1R,3aS,3bS,10aS,10bR,11S,12aS)-10b-Fluoro-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic acid

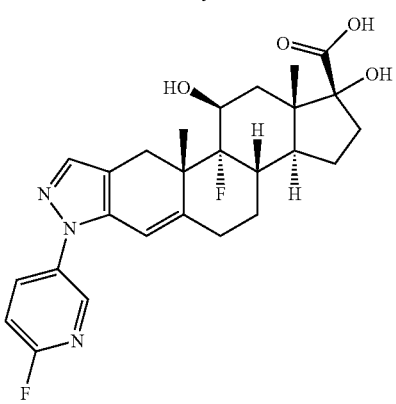

In a 500 mL round-bottomed flask was dissolved intermediate 19 (10 g, 25.35 mmol) in acetic acid (100 mL) and the solution was degassed with nitrogen for 5 minutes. 2-Fluoro-5-hydrazinylpyridine (3.22 g, 25.35 mmol) was added at room temperature and the obtained mixture was stirred for 15 minutes. The resulting solution was freeze-dried overnight and the resulting material was suspended in EtOAc (40 ml) and stirred at room temperature for another 10 minutes. The resulting solid was isolated by filtration, washed with EtOAc (10 ml) and was finally dried in a stream of air on the glass-filter funnel to yield 6.9 g of the desired product as a solid. APCI-MS m/z: 486 [MH+].

Intermediate 21

(1R,3aS,3bS,10aS,10bR,11S,12aS)-10b-Fluoro-7-(6-fluoropyridin-3-yl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid

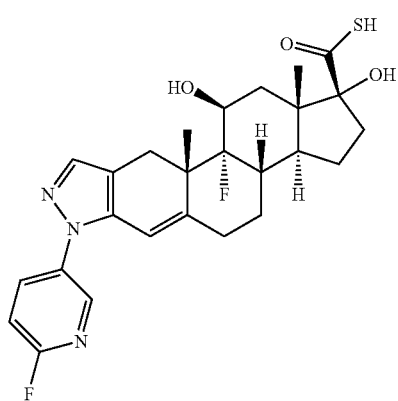

The compound was prepared according to the description for intermediate 5, starting from intermediate 20. APCI-MS m/z: 502 [MH+].

Intermediate 22

(1R,3aS,3bS,10aS,10bR,11S,12aS)-10b-Fluoro-7-(6-fluoropyridin-3-yl)-11-hydroxy-10a,12a-dimethyl-1-{[(2R)-tetrahydrofuran-2-ylcarbonyl]oxy}-1,2,3,3a,3b,4,5,7,10,10a,10b,11,12,12a-tetradecahydrocyclopenta[5,6]naphtho[1,2-f]indazole-1-carbothioic S-acid

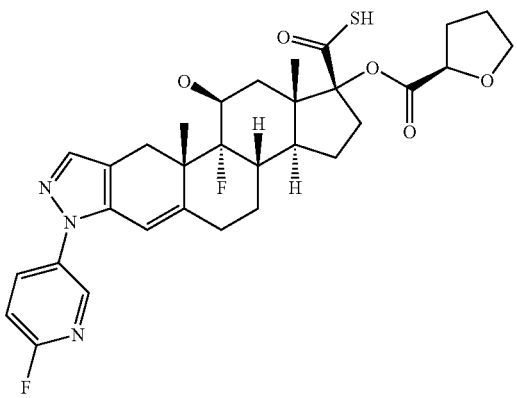

Intermediate 21 (0.3 g, 0.6 mmol) was dissolved in DCM (10 ml) and triethylamine (0.165 ml, 1.2 mmol) was added at room temperature. The mixture was stirred for 3 min. before (R)-tetrahydrofuran-2-carbonyl chloride (J. Chem. Soc, Perkin Trans. 1, 2002, 571-576) (0.15 g, 1.2 mmol) in DCM (1 ml) was added portionwise and the mixture was stirred for 15 min. $N_1$-ethyl-$N_2$,$N_2$-dimethylethane-1,2-diamine (0.305 ml, 2.04 mmol) was added and the mixture was stirred for another 20 min. The mixture was diluted with DCM (20 ml), washed with 2N HCl (2 times 20 ml), brine and dried over sodium sulfate. Filtration and evaporation of the solvent under reduced pressure gave 0.4 g of crude product which was used as such without any further purification. APCI-MS m/z: 600 [MH+].

Intermediate 23

(1R,3aS,3bS,10aS,10bR,11S,12aS)-10b-Fluoro-7-(6-fluoropyridin-3-yl)-11-hydroxy-10a,12a-dimethyl-1-[(tetrahydrofuran-3-ylcarbonyl)oxy]-1,2,3,3a,3b,4,5,7,10,10a,10b,11,12,12a-tetradecahydrocyclopenta[5,6]naphtho[1,24]indazole-1-carbothioic S-acid

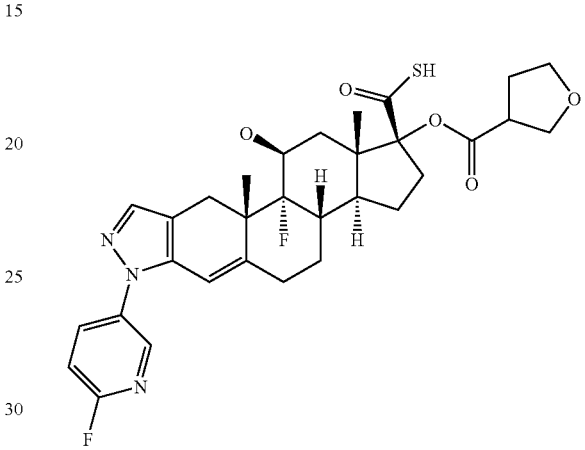

The compound was prepared according to the procedure for Intermediate 22, starting from Intermediate 21. APCI-MS m/z: 600 [MH+].

Intermediate 24

(1R,3aS,3bS,10aS,10bR,11S,12aS)-10b-Fluoro-7-(6-fluoropyridin-3-yl)-11-hydroxy-10a,12a-dimethyl-1-{[(2S)-tetrahydrofuran-2-ylcarbonyl]oxy}-1,2,3,3a,3b,4,5,7,10,10a,10b,11,12,12a-tetradecahydrocyclopenta[5,6]naphtho[1,2-f]indazole-1-carbothioic S-acid

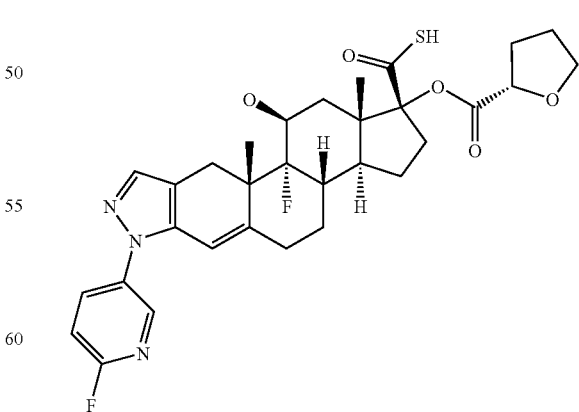

The compound was prepared according to the procedure for Intermediate 22, starting from Intermediate 21. APCI-MS m/z: 600 [MH+].

Intermediate 25

(8S,9S,10R,11S,13S,14S,17R)-11,17-Dihydroxy-10,
13-dimethyl-3-oxo-2,3,6,7,8,9,10,11,12,13,14,15,16,
17-tetradecahydro-1H-cyclopenta[a]phenanthrene-
17-carboxylic acid

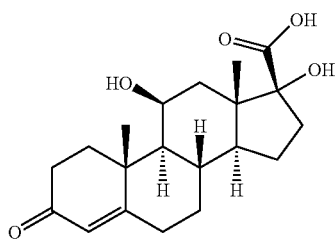

In a 1000 mL round-bottomed flask was suspended (8S, 9S,10R,11S,13S,14S,17R)-11,17-dihydroxy-17-(2-hydroxyacetyl)-10,13-dimethyl-6,7,8,9,10,11,12,13,14,15,16,17-dodecahydro-1H-cyclopenta[a]phenanthren-3(2H)-one (10.4 g, 28.69 mmol) in MeOH (200 mL) and a solution of orthoperiodic acid (9.81 g, 43.04 mmol) in water (200 mL) was added to give a colorless solution. The mixture was stirred for 45 minutes after which an additional 3 g of orthoperiodic acid was added and stirring was continued for another hour. MeOH was removed in vacuo and the residual aqueous mixture was diluted with 200 ml of water. The resulting solid was isolated by filtration and was air-dried on the sinter to yield 8.1 g of the desired compound as a white solid. APCI-MS m/z: 349 [MH$^+$].

Intermediate 26

(8S,9S,10R,11S,13S,14S,17R)-2-Formyl-11,17-dihydroxy-10,13-dimethyl-3-oxo-2,3,6,7,8,9,10,11,12,13,14,15,16,17-tetradecahydro-1H-cyclopenta[a]phenanthrene-17-carboxylic acid

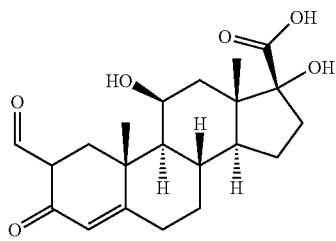

To a stirred suspension of sodium hydride (5.73 g, 143.5 mmol, 60% suspension in mineral oil) in THF (100 ml) under argon was added intermediate 25 (5.00 g, 14.35 mmol) in small portions. After 5 minutes ethyl formate (58.4 ml, 717.5 mmol) was added and stirring was continued at room temperature overnight. The mixture was quenched with formic acid to afford a thick suspension and aqueous NaOH solution (2M, 50 ml) was added. The mixture was stirred at room temperature for 10 min, the layers were separated and the organic layer was discarded. The aqueous layer was acidified with aqueous conc. HCl and extracted with ethyl acetate (3 times 50 ml). The combined organic phases were dried with sodium sulfate, filtered and the solvent evaporated under reduced pressure to afford the target compound as a yellow solid (5.65 g). APCI-MS m/z: 377 [MH$^+$].

Intermediate 27

(1R,3aS,3bS,10aR,10bS,11S,12aS)-7-(4-Fluorophenyl)-1,10-dihydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic acid

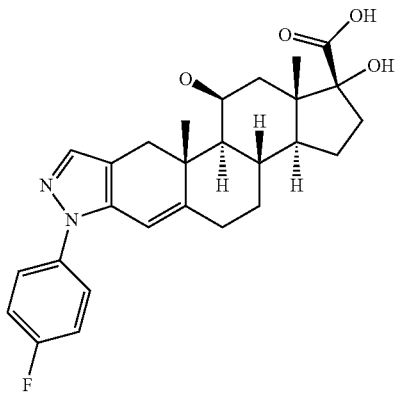

Intermediate 26 (4.2 g, 11.16 mmol) was dissolved in acetic acid (30 mL) and (4-fluorophenyl)hydrazine hydrochloride (2.177 g, 13.39 mmol) followed by sodium acetate (0.783 mL, 14.50 mmol) were added followed by dilution with water (8 ml). After stirring at room temperature for 2 hours, the mixture was concentrated in vacuo and the liquid residue was poured into EtOAc (200 ml) and water (150 ml). The aqueous phase was removed and the organic phase was washed with 2M NaOH (3×90 ml) and the combined aqueous phases were acidified and extracted with EtOAc (3 times 100 ml). The combined organic phases were washed with brine (100 ml), dried over Na$_2$SO$_4$ and concentrated in vacuo to yield 4.2 g of the target compound as a light brown foam. APCI-MS m/z: 467 [MH$^+$].

Intermediate 28

(1R,3aS,3bS,10aR,10bS,11S,12aS)-7-(4-Fluorophenyl)-1,11-dihydroxy-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid

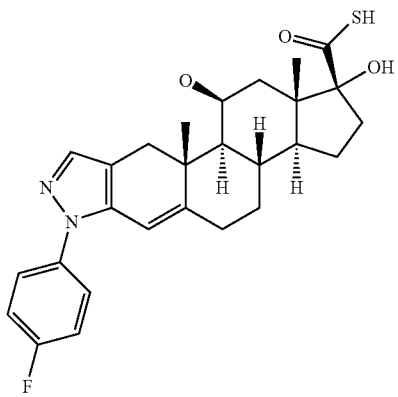

In a 25 ml round-bottomed flask intermediate 27 (0.2 g, 0.43 mmol) was dissolved in DMF (3 ml) and 1,1-carbonyldiimidazole (0.139 g, 0.86 mmol) was added. The resulting solution was stirred overnight at room temperature. H$_2$S (g) was bubbled through the solution for 5 minutes and the mixture was stirred for an additional 30 minutes. The reaction mixture was poured into 1M HCl (15 ml) and the solid formed was isolated by filtration, washed with water and dried to give 0.2 g of the crude desired compound which was taken on as such without any further purification. APCI-MS m/z: 483 [MH$^+$].

Intermediate 29

(1R,3aS,3bS,10aR,10bS,11S,12aS)-7-(4-Fluorophenyl)-11-hydroxy-10a,12a-dimethyl-1-[(tetrahydrofuran-2-ylcarbonyl)oxy]-1,2,3,3a,3b,4,5,7,10,10a,10b,11,12,12a-tetradecahydrocyclopenta[5,6]naphtho[1,2-f]indazole-1-carbothioic S-acid

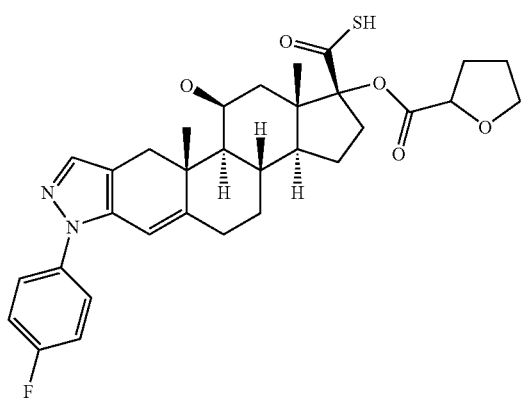

The compound was prepared from Intermediate 28 and tetrahydrofuran-2-carbonyl chloride (J. Chem. Soc, Perkin Trans. 1, 2002, 571-576) according to the procedure for Intermediate 22. APCI-MS m/z: 581 [MH⁺].

Intermediate 30

(1R,3aS,3bS,10aS,10bR,11S,12aS)-1-[(Cyclopropylcarbonyl)oxy]-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic acid

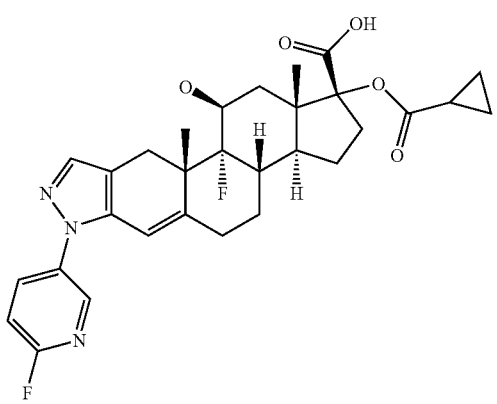

Intermediate 20 (0.1 g, 0.21 mmol) was dissolved in DCM (4 mL), triethylamine (0.09 ml, 0.65 mmol) was added and the mixture was stirred for 5 minutes before cyclopropanecarbonyl chloride (0.035 ml, 0.39 mmol) in DCM (1 ml) was added at room temperature and the mixture was stirred for 30 minutes. $N_1,N_1,N_2$-trimethylethane-1,2-diamine (0.12 ml, 0.94 mmol) was added and the mixture was stirred for another 25 minutes at the same temperature. The reaction mixture was diluted with DCM (10 ml) and washed with 1M HCl(2×10 ml) and brine (20 ml). The organic phase was dried over $Na_2SO_4$, filtered and evaporated in vacuo to yield 110 mg of the target compound. APCI-MS m/z: 554 [MH⁺].

Intermediate 31

(1R,3aS,3bS,10aR,10bS,11S,12aS)-1-[(Cyclopropylcarbonyl)oxy]-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazole-1-carboxylic acid

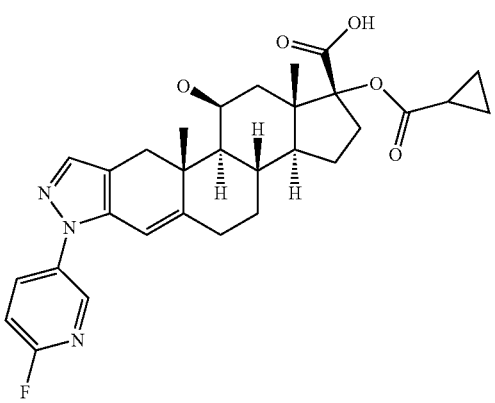

The compound was prepared according to the procedure for intermediate 27 and intermediate 30, starting from intermediate 26 and cyclopropanecarbonyl chloride. APCI-MS m/z: 536 [MH⁺].

Intermediate 32

(1R,3aS,3bS,5S,10aR,10bS,11S,12aS)-7-(6-Fluoropyridin-3-yl)-1-[(furan-2-ylcarbonyl)oxy]-11-hydroxy-5,10a,12a-trimethyl-1,2,3,3a,3b,4,5,7,10,10a,10b,11,12,12a-tetradecahydrocyclopenta[5,6]naphtho[1,2-f]indazole-1-carbothioic S-acid

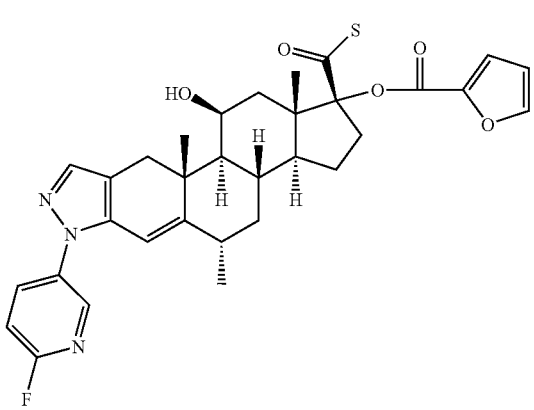

The compound was prepared according to the description for intermediate 6, starting from intermediate 13. APCI-MS m/z: 592 [MH⁺].

EXAMPLE 1

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate

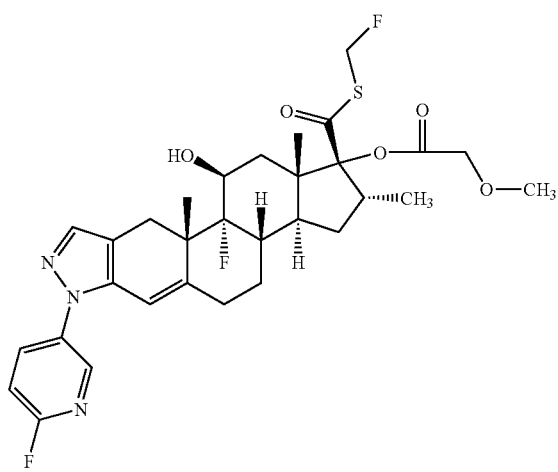

In a 250 mL round-bottomed flask was dissolved intermediate 5 (8.8 g, 17.07 mmol) in DCM (80 mL) and triethylamine (5.91 mL, 42.67 mmol) was added. To the stirred mixture was added 2-methoxyacetyl chloride (3.89 g, 35.84 mmol), whilst cooling in a water bath, and the mixture was stirred for 10 minutes. $N_1$-ethyl-$N_2$,$N_2$-dimethylethane-1,2-diamine (3.48 mL, 22.19 mmol) was added and the mixture was stirred for another 10 minutes A solution of 60% bromofluoromethane (4.82 g, 25.60 mmol) in DMF was added, followed by triethyl amine (2 ml) and the reaction was allowed to stir for an additional 30 minutes. The resulting mixture was concentrated in vacuo and partitioned between EtOAc (150 ml) and 1M HCl (150 ml). The aqueous phase was extracted with EtOAc (150 ml) and the combined organic phases were washed with 0.5M HCl(2×100 ml), water (100 ml) and brine (50 ml). Drying over $Na_2SO_4$ was followed by filtration and evaporation in vacuo to yield the crude product as a foam which was purified on silica (Heptane:EtOAc 3:1 to 2:1) to give 2.9 g of the target compound as a yellowish solid.

A small sample (0.35 g) of this material was purified on a preparative HPLC column (Kromasil C18, CH3CN/water), the compound containing fraction were freeze-dried to yield 0.26 g of the target compound as a colourless solid. The solid was suspended in $Et_2O$ (10 ml) and the suspension was stirred at room temperature for 2 hours. The solid was isolated by filtration to give 0.23 g of the tartet compound as a white crystalline solid. APCI-MS m/z: 620 [MH$^+$].

$^1$H NMR (400 MHz, CDCl$_3$) δ 8.36 (1H, s), 7.99 (1H, m), 7.51 (1H, s), 7.07 (1H, dd), 6.18 (1H, s), 6.01-5.76 (2H, m), 4.45 (1H, bs), 4.12 (2H, s), 3.45 (3H, s), 3.45-3.40 (1H, m), 3.32 (1H, d), 2.80 (1H, m), 2.61 (1H, t), 2.49-2.19 (4H, m), 1.96-1.82 (2H, m), 1.76-1.66 (1H, m), 1.65-1.51 (1H, m), 1.41 (3H, s), 1.41-1.33 (1H, m), 1.28 (1H, bs), 1.12 (3H, s), 1.04 (3H, d).

EXAMPLE 2

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate

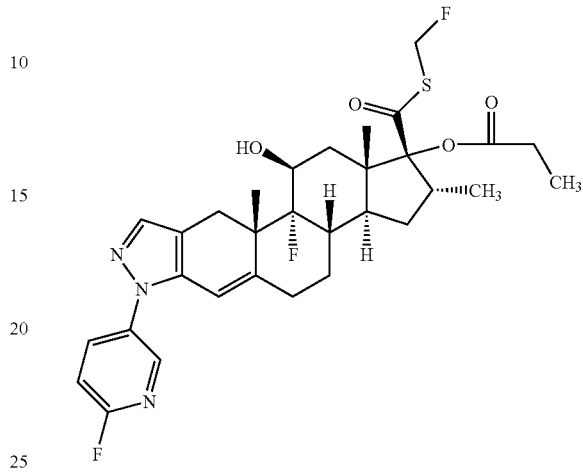

In a vial was dissolved intermediate 6 (0.05 g, 0.09 mmol) and N,N-diisopropyl ethylamine (0.043 mL, 0.26 mmol) in dioxane (3 mL) and a 60% solution of bromofluoromethane (0.033 g, 0.17 mmol) in DMF was added at room temperature. The mixture was stirred for 60 minutes and the resulting crude mixture was concentrated in vacuo, dissolved in $CH_3CN$/water (3 ml/0.5 ml), and was injected onto a preparative HPLC-column. The product containing fractions were freeze-dried to give 15 mg of the desired compound as a colourless solid. APCI-MS m/z: 604 [MH$^+$].

$^1$H NMR (400 MHz, CDCl$_3$) δ 8.36 (1H, s), 7.99 (1H, m), 7.50 (1H, s), 7.07 (1H, m), 6.18 (1H, s), 6.03-5.75 (2H, m), 4.45 (1H, bs), 3.41 (1H, bs), 3.33 (1H, d), 2.81 (1H, d), 2.61 (1H, t), 2.52-2.32 (5H, m), 2.32-2.21 (1H, m), 1.96-1.80 (2H, m), 1.77-1.66 (1H, m), 1.65-1.51 (1H, m), 1.41 (3H, s), 1.41-1.32 (1H, m), 1.29 (1H, bs), 1.17 (3H, t), 1.10 (3H, s), 1.01 (3H, d).

EXAMPLE 3

(1R,2R,3aS,3bS,10aS,10bR,11S,12aS)-1-{[(Cyanomethyl)sulfanyl]carbonyl}-10b-fluoro-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate

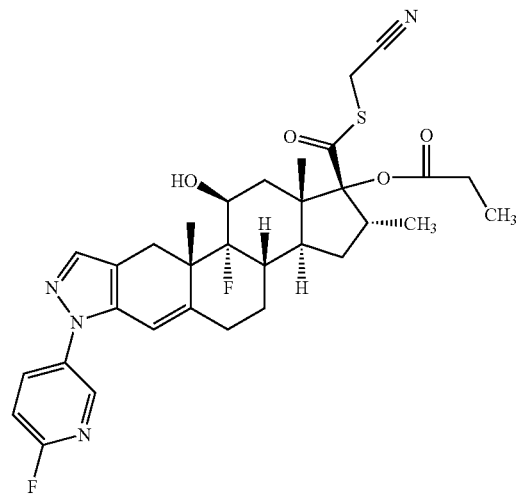

In a vial was dissolved intermediate 6 (0.05 g, 0.09 mmol) and N,N-diisopropyl-ethylamine (0.020 mL, 0.12 mmol) in dioxane (3 mL) and 2-bromoacetonitrile (6.99 μL, 0.10 mmol) was added at room temperature. The mixture was stirred for 10 minutes, the volatiles were removed in vacuo and the residue was suspended in CH₃CN (3 ml) and water (1 ml). The obtained suspension was filtered and the solution was injected onto a preparative HPLC-column. The product containing fractions were combined and freeze-dried to give 8 mgs of the desired compound as a colourless solid. APCI-MS m/z: 611 [MH⁺].

¹H NMR (400 MHz, CDCl₃) δ 8.36 (1H, s), 7.99 (1H, m), 7.51 (1H, s), 7.07 (1H, dd), 6.18 (1H, s), 4.46 (1H, bs), 3.72 (2H, s), 3.41-3.28 (2H, m), 2.81 (1H, d), 2.61 (1H, t), 2.48-2.31 (5H, m), 2.31-2.18 (1H, m), 1.94-1.80 (2H, m), 1.77-1.66 (1H, m), 1.65-1.51 (1H, m), 1.44 (1H, bs), 1.41 (3H, s), 1.41-1.32 (1H, m), 1.16 (3H, t), 1.12 (3H, s), 1.02 (3H, d).

EXAMPLE 4

(1R,2R,3aS,3bS,10aS,10bR,11S,12aS)-10b-Fluoro-1-{[(fluoromethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate

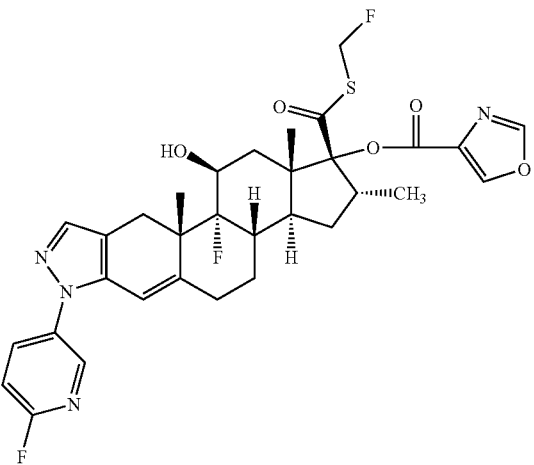

The compound was prepared according to the description in Example 2, starting from intermediate 7. APCI-MS m/z: 643 [MH⁺].

¹H NMR (400 MHz, CDCl₃) δ 8.37 (1H, s), 8.25 (1H, s), 7.99 (1H, m), 7.95 (1H, s), 7.51 (1H, s), 7.08 (1H, dd), 6.19 (1H, s), 6.05-5.74 (2H, m), 4.51 (1H, bs), 3.57-3.45 (1H, m), 3.37 (1H, d), 2.82 (1H, d), 2.69-2.51 (2H, m), 2.46-2.23 (3H, m), 2.03-1.85 (2H, m), 1.81-1.70 (1H, m), 1.66-1.56 (1H, m), 1.43 (3H, s), 1.42-1.32 (2H, m), 1.17 (3H, s), 1.08 (3H, d).

EXAMPLE 5

(1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate

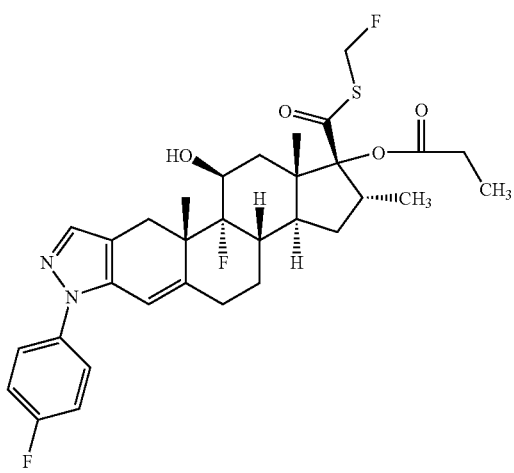

In a 50 mL round-bottomed flask was dissolved intermediate 8 (0.09 g, 0.17 mmol) and triethylamine (0.061 mL, 0.44 mmol) in DCM (10 mL) and propionyl chloride (0.034 g, 0.37 mmol) was added at room temperature. The mixture was stirred for 10 minutes and N₁-ethyl-N₂,N₂-dimethylethane-1,2-diamine (0.082 mL, 0.52 mmol) was added and the mixture was stirred for an additional 10 minutes. The reaction mixture was diluted with DCM up to a total volume of 25 ml and the resulting mixture was washed with 1M HCl (2×20 ml) and brine (10 ml). The organic phase was dried over Na₂SO₄, filtered and evaporated to give 90 mg of (1R,2R,3aS,3bS,10aS,10bR,11S,12aS)-10b-fluoro-7-(6-fluoropyridin-3-yl)-11-hydroxy-2,10a,12a-trimethyl-1-(propanoyloxy)-1,2,3,3a,3b,4,5,7,10,10a,10b,11,12,12a-tetradecahydrocyclopenta[5,6]naphtho[1,2-f]indazole-1-carbothioic S-acid as a yellow solid. APCI-MS m/z: 571 [MH⁺].

The obtained carbothioic acid (0.045 g, 0.08 mmol) and N,N-diisopropyl-ethylamine (0.039 mL, 0.24 mmol) were dissolved in dioxane (3 mL) and a 60% solution of bromofluoromethane (0.030 g, 0.16 mmol) in DMF was added. The mixture was stirred for 60 minutes and the volatiles were subsequently removed in vacuo. The residue was suspended in a mixture of CH₃CN (3 ml) and water (1 ml) and the obtained suspension was filtered and the solution was injected onto a preparative HPLC-column. The product containing fractions were combined and freeze-dried to give 15 mgs of the desired compound as a colourless solid. APCI-MS m/z: 603 [MH⁺].

¹H NMR (400 MHz, CDCl₃) δ 7.50-7.42 (3H, m), 7.16 (2H, t), 6.18 (1H, s), 6.02-5.75 (2H, m), 4.45 (1H, bs), 3.41 (1H, bs), 3.32 (1H, d), 2.79 (1H, d), 2.59 (1H, t), 2.51-2.38 (3H, m), 2.38-2.18 (3H, m), 1.97-1.79 (2H, m), 1.75-1.65 (1H, m), 1.63-1.51 (1H, m), 1.40 (3H, s), 1.39-1.32 (1H, m), 1.32-1.27 (1H, m), 1.17 (3H, t), 1.10 (3H, s), 1.01 (3H, d).

EXAMPLE 6

(1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate

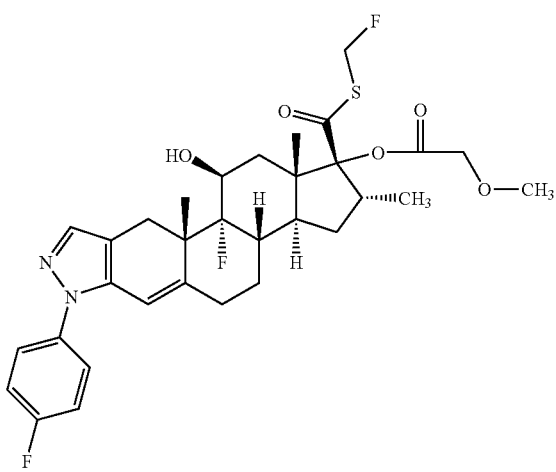

In a 50 mL round-bottomed flask was dissolved intermediate 8 (0.09 g, 0.17 mmol) and triethylamine (0.061 mL, 0.44 mmol) in DCM (10 mL) and 2-methoxyacetyl chloride (0.040 g, 0.37 mmol) was added at room temperature. The mixture was stirred for 10 minutes, $N_1$-ethyl-$N_2$,$N_2$-dimethylethane-1,2-diamine (0.082 mL, 0.52 mmol) was added and the resulting mixture was stirred for another 10 minutes. The reaction mixture was diluted with DCM up to a total volume of 25 ml, and washed with 1M HCl(2×20 ml) and brine (10 ml). The organic phase was dried over $Na_2SO_4$, filtered and evaporated to give 105 mg of (1R,3aS,3bS,5S,10aR,10bS,11S,12aS)-7-(6-fluoropyridin-3-yl)-11-hydroxy-1-[(methoxyacetyl)oxy]-10a,12a-dimethyl-1,2,3,3a,3b,4,5,7,10,10a,10b,11,12,12a-tetradecahydrocyclopenta[5,6]naphtho[1,2-f]indazole-1-carbothioic S-acid as a yellow solid. APCI-MS m/z: 587 [MH$^+$].

The obtained carbothioic acid (0.05 g, 0.09 mmol) and N,N-diisopropyl-ethylamine (0.042 mL, 0.26 mmol) were dissolved in dioxane (3 mL) and a 60% solution of bromofluoromethane (0.032 g, 0.17 mmol) in DMF was added at room temperature. The obtained mixture was stirred for 60 minutes, the volatiles were removed in vacuo and the residue was suspended in $CH_3CN$ (3 ml) and water (1 ml) was added. The suspension was filtered and the solution was injected onto a preparative HPLC-column. The product containing fractions were combined and freeze-dried to give 12 mg of the desired compound as a white solid. APCI-MS m/z: 619 [MH$^+$].

$^1$H NMR (400 MHz, CDCl$_3$) δ 7.50-7.42 (3H, m), 7.16 (2H, t), 6.17 (1H, s), 6.01-5.76 (2H, m), 4.45 (1H, bs), 4.12 (2H, s), 3.46 (3H, s), 3.50-3.38 (1H, m), 3.31 (1H, d), 2.78 (1H, d), 2.59 (1H, t), 2.47-2.18 (4H, m), 1.95-1.81 (2H, m), 1.75-1.64 (1H, m), 1.63-1.51 (1H, m), 1.40 (3H, s), 1.39-1.29 (2H, m), 1.11 (3H, s), 1.04 (3H, d).

EXAMPLE 7

(1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate

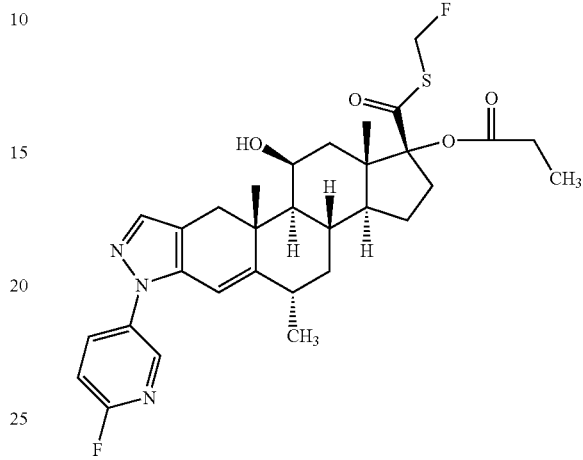

The compound was prepared according to the description in Example 2, starting from intermediate 14. APCI-MS m/z: 586 [MH$^+$].

$^1$H NMR (400 MHz, CDCl$_3$) δ 8.37 (1H, s), 8.01 (1H, m), 7.49 (1H, s), 7.09 (1H, dd), 6.12 (1H, s), 6.06-5.61 (2H, m), 4.57 (1H, bs), 3.06-2.95 (2H, m), 2.77 (1H, d), 2.54 (1H, bs), 2.37 (2H, m), 2.18-2.06 (2H, m), 2.04-1.91 (3H, m), 1.87-1.76 (1H, m), 1.68-1.58 (1H, m), 1.54-1.41 (1H, m), 1.34 (3H, s), 1.26 (1H, d), 1.20-1.08 (7H, m), 1.01 (3H, s), 0.87 (1H, q).

EXAMPLE 8

(1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate

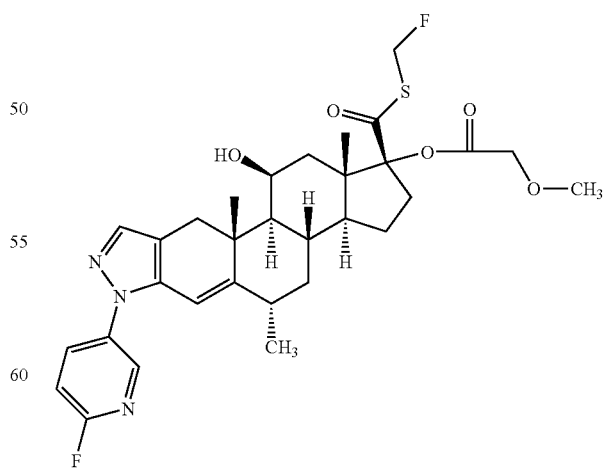

The compound was prepared according to the description in Example 2, starting from intermediate 15. APCI-MS m/z: 602 [MH$^+$].

¹H NMR (400 MHz, CDCl₃) δ 8.37 (1H, s), 8.01 (1H, m), 7.49 (1H, s), 7.09 (1H, dd), 6.12 (1H, s), 6.05-5.63 (2H, m), 4.57 (1H, bs), 4.06 (2H, s), 3.46 (3H, s), 3.10-2.96 (2H, m), 2.77 (1H, d), 2.54 (1H, bs), 2.19-1.91 (5H, m), 1.90-1.77 (1H, m), 1.67-1.42 (2H, m), 1.34 (3H, s), 1.26 (1H, d), 1.15-1.09 (4H, m), 1.01 (3H, s), 0.86 (1H, q).

EXAMPLE 9

(1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate

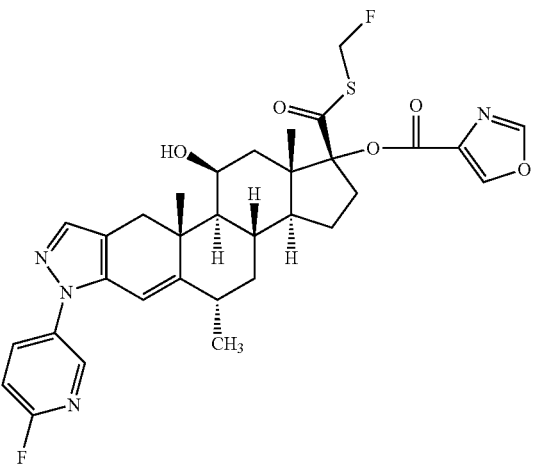

The compound was prepared according to the description in Example 2, starting from intermediate 16. APCI-MS m/z: 625 [MH⁺].

¹H NMR (400 MHz, CDCl₃) δ 8.37 (1H, s), 8.31 (1H, s), 8.01 (1H, m), 7.96 (1H, s), 7.50 (1H, s), 7.09 (1H, dd), 6.12 (1H, s), 6.07-5.60 (2H, m), 4.64 (1H, bs), 3.17-3.06 (1H, m), 3.03 (1H, d), 2.81 (1H, d), 2.55 (1H, bs), 2.28 (1H, d), 2.22-2.05 (3H, m), 1.96 (1H, m), 1.92-1.80 (1H, m), 1.80-1.69 (1H, m), 1.59-1.47 (1H, m), 1.36 (3H, s), 1.34 (1H, s), 1.15 (1H, d), 1.11 (3H, d), 1.06 (3H, s), 0.90 (1H, q).

EXAMPLE 10

(1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate

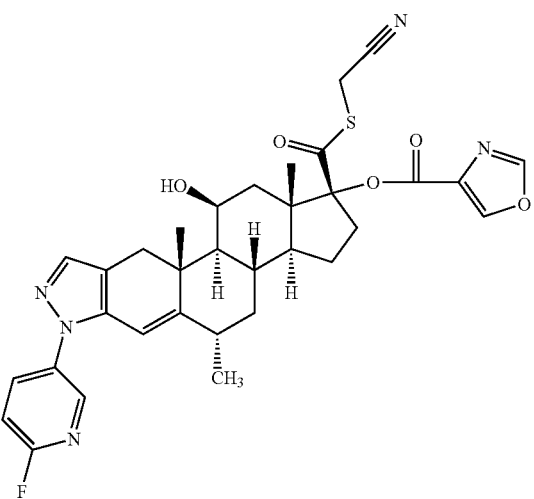

The compound was prepared according to the description in Example 3, starting from intermediate 16. APCI-MS m/z: 632 [MH⁺].

¹H NMR (400 MHz, CDCl₃) δ 8.37 (1H, s), 8.31 (1H, s), 8.01 (1H, m), 7.96 (1H, s), 7.50 (1H, s), 7.09 (1H, dd), 6.12 (1H, s), 4.64 (1H, bs), 3.80 (1H, d, AB), 3.56 (1H, d, AB), 3.14-2.99 (2H, m), 2.81 (1H, d), 2.55 (1H, bs), 2.26 (1H, d), 2.22-2.10 (2H, m), 2.06 (1H, d), 1.96 (1H, m), 1.92-1.80 (1H, m), 1.79-1.67 (1H, m), 1.61-1.48 (1H, m), 1.36 (3H, s), 1.33 (1H, s), 1.22 (1H, s), 1.11 (3H, d), 1.07 (3H, s), 0.89 (1H, q).

EXAMPLE 11

(1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate

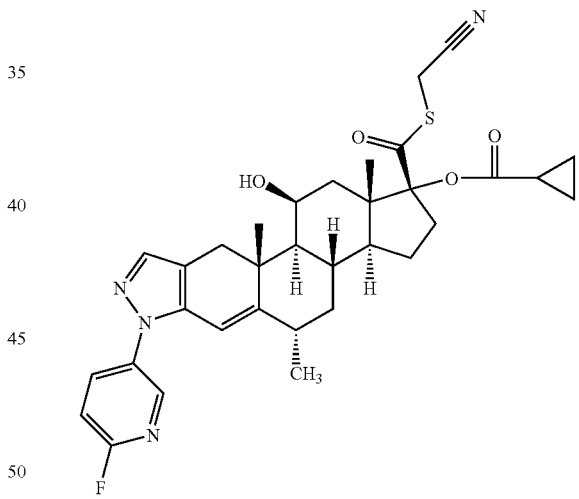

The compound was prepared according to the description in Example 3, starting from intermediate 17. APCI-MS m/z: 605 [MH⁺].

¹H NMR (400 MHz, CDCl₃) δ 8.37 (1H, s), 8.01 (1H, m), 7.50 (1H, s), 7.09 (1H, dd), 6.12 (1H, s), 4.58 (1H, bs), 3.78 (1H, d, AB), 3.56 (1H, d, AB), 3.02 (1H, d), 2.96 (1H, m), 2.77 (1H, d), 2.54 (1H, bs), 2.19-2.06 (2H, m), 2.03-1.91 (3H, m), 1.90-1.78 (1H, m), 1.71-1.60 (2H, m), 1.54-1.41 (1H, m), 1.35 (3H, s), 1.27 (1H, d), 1.16 (1H, d), 1.12 (3H, d), 1.08-0.98 (5H, m), 0.97-0.83 (3H, m).

EXAMPLE 12

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate

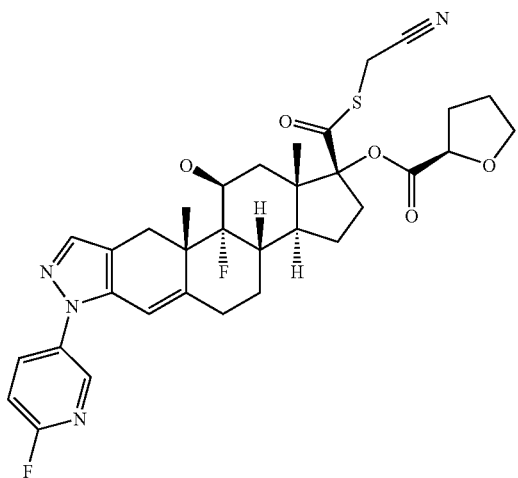

Intermediate 22 (0.04 g, 0.07 mmol) was dissolved in dioxane (1 mL) to give a yellow solution. N-ethyl-N-isopropylpropan-2-amine (0.03 mL, 0.18 mmol) and 2-bromoacetonitrile (20 μL, 0.03 mmol) were added, and the mixture was stirred overnight. The solution was diluted with $CH_3CN$ (1 ml) and water (1 ml), and was then injected into a preparative HPLC column ($CH_3CN$/water). The product-containing fraction was freeze-dried to give 10 mg of the desired product as a white solid. APCI-MS m/z: 634 [MH$^+$].

$^1$H NMR (400 MHz, DMSO) δ 8.40 (d, 1H), 8.17 (t, 1H), 7.57 (s, 1H), 7.35 (d, 1H), 6.25 (s, 1H), 5.34 (s, 1H), 4.53-4.40 (m, 1H), 4.31 (s, 1H), 4.03 (dd, 2H), 3.80 (m, 2H), 3.13 (d, 1H), 2.81 (m, 1H), 2.42-2.13 (m, 2H), 2.10-1.77 (m, 6H), 1.70 (m, 2H), 1.48-1.29 (m, 5H), 0.98 (s, 3H).

EXAMPLE 13

(1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2R)-tetrahydrofuran-2-carboxylate

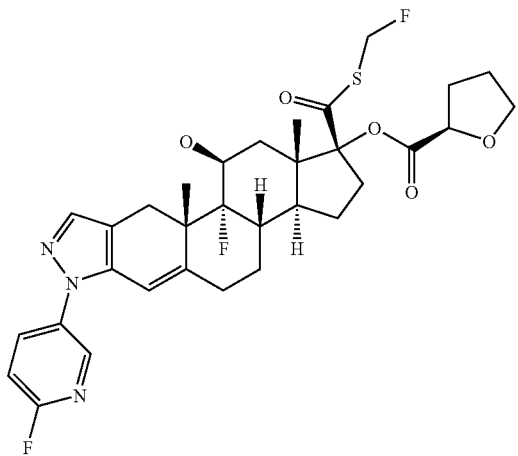

The compound was prepared according to the procedure for Example 12 starting from Intermediate 22 and bromofluoromethane. APCI-MS m/z: 632 [MH$^+$].

$^1$H NMR (400 MHz, DMSO) δ 8.40 (d, 1H), 8.15 (s, 1H), 7.62 (s, 1H), 7.36 (dd, 1H), 6.28 (s, 1H), 6.03-5.93 (m, 1H), 5.90-5.80 (m, 1H), 5.30 (s, 1H), 4.47 (dd, 1H), 4.31 (s, 1H), 3.86-3.74 (m, 2H), 3.14 (d, 1H), 2.81 (d, 2H), 2.41-2.13 (m, 5H), 2.11-1.77 (m, 7H), 1.77-1.62 (m, 1H), 1.48-1.27 (m, 4H), 0.95 (s, 3H).

EXAMPLE 14

(1R,3aS,3bS,10aS,10bR,11S,12aS)-10b-Fluoro-7-(6-fluoropyridin-3-yl)-11-hydroxy-1-{[(2-hydroxyethyl)sulfanyl]carbonyl}-10a,12a-dimethyl-1,2,3,3a,3b,4,5,7,10,10a,10,11,12,12a-tetradecahydrocyclopenta[5,6]naphtho[1,2-f]indazol-1-yl (2R)-tetrahydrofuran-2-carboxylate

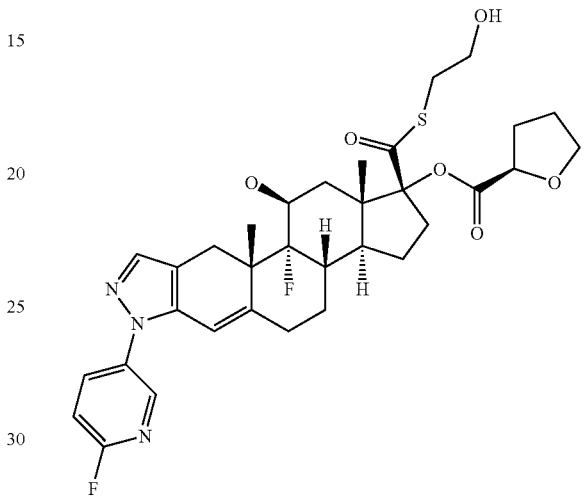

The compound was prepared according to the procedure for Example 12 starting from Intermediate 22 and 2-Bromoethanol. APCI-MS m/z: 644 [MH$^+$].

$^1$H NMR (400 MHz, DMSO) δ 8.40 (d, 1H), 8.15 (d, 1H), 7.57 (s, 1H), 7.35 (dd, 1H), 6.24 (1, 1H), 5.17 (s, 1H), 4.43 (dd, 1H), 4.28 (m, 2H), 3.87-3.70 (m, 4H), 3.14 (d, 1H), 2.99-2.72 (m, 4H), 2.40-1.95 (m, 6H), 1.94-1.60 (m, 7H), 1.46-1.24 (m, 4H), 0.95 (s, 3H).

EXAMPLE 15

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate

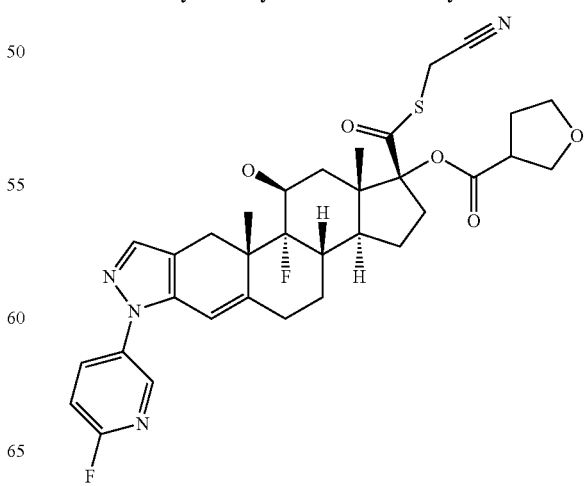

The compound was prepared according to the procedure for Example 12 starting from Intermediate 23 and 2-Bromoacetonitrile. APCI-MS m/z: 639 [MH+].

¹H NMR (400 MHz, DMSO) δ 8.40 (s, 1H), 8.15 (dd, 1H), 7.61 (s, 1H), 7.36 (dd, 1H), 6.29 (s, 1H), 5.29 (d, 1H), 4.32 (s, 1H), 4.03 (dd, 2H), 3.89-3.63 (m, 4H), 3.25-3.08 (m, 2H), 2.88-2.71 (m, 2H), 2.42-2.14 (m, 4H), 2.13-1.61 (m, 7H), 1.50-1.28 (m, 5H), 0.92 (s, 3H).

A mixture of isomers was obtained and the isomers were separated on a chiralpak IA column (i-hexane/EtOH=1:1) and two peaks were analyzed.

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate The above compound was the first eluting isomer on a chiralpak IA column (i-hexane/EtOH=1:1). APCI-MS m/z: 639 [MH+].

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate The above compound was the second eluting isomer on a chiralpak IA column (i-hexane/EtOH=1:1). APCI-MS m/z: 639 [MH+].

EXAMPLE 16

(1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl tetrahydrofuran-3-carboxylate

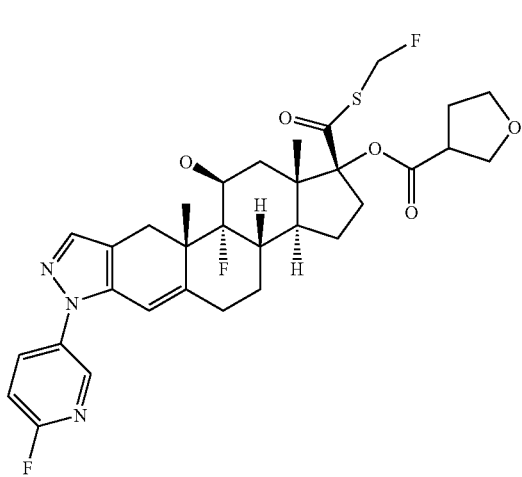

The compound was prepared according to the procedure for Example 12 starting from Intermediate 23 and Bromofluoromethane. APCI-MS m/z: 632 [MH+].

¹H NMR (400 MHz, DMSO) δ 8.40 (d, 1H), 8.15 (t, 1H), 7.63 (s, 1H), 7.36 (d, 1H), 6.32 (s, 1H), 6.02-5.94 (m, 1H), 5.89-5.81 (m, 1H), 5.24 (d, 1H), 4.31 (s, 1H), 3.62-3.90 (m, 4H), 3.08-3.26 (m, 2H), 2.71-2.88 (m, 3H), 2.29-2.41 (m, 2H), 1.97-2.14 (m, 6H), 1.78-1.96 (m, 2H), 1.61-1.77 (m, 1H), 1.29-1.48 (m, 4H), 0.90 (s, 3H).

A mixture of isomers was obtained and the isomers were separated on a chiralpak IA column (i-hexane/EtOH=1:1) and two peaks were analyzed.

(1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (R)/(S) tetrahydrofuran-3-carboxylate The above compound was the first eluting isomer on a chiralpak IA column (i-hexane/EtOH=1:1). APCI-MS m/z: 632 [MH+].

(1R,3aS,3bS,10aS,10bR,11S,12aS)-10b-Fluoro-1-{[(fluoromethyl)sulfanyl]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-3-carboxylate The above compound was the second eluting isomer on a chiralpak IA column (i-hexane/EtOH=1:1). APCI-MS m/z: 632 [MH+].

EXAMPLE 17

(1R,3aS,3bS,10aS,10bR,11S,12aS)-1-{[(Cyanomethyl)sulfanyl]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl (2S)-tetrahydrofuran-2-carboxylate

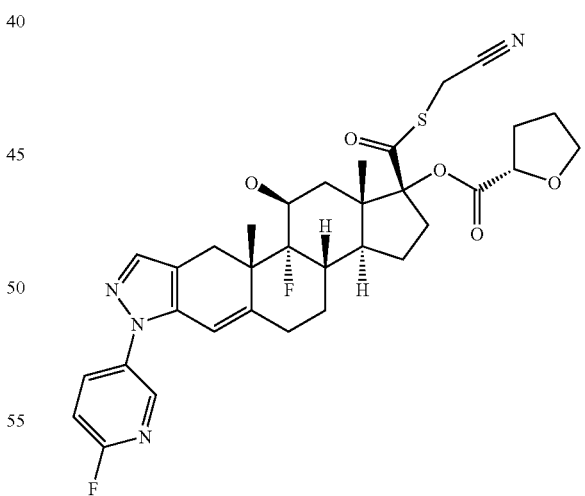

The compound was prepared according to the procedure for Example 12, starting from Intermediate 24 and 2-Bromoacetonitrile. APCI-MS m/z: 639 [MH+].

¹H NMR (400 MHz, DMSO) δ 8.45 (s, 1H), 8.15 (dd, 1H), 7.66 (s, 1H), 7.36 (dd, 1H), 6.30 (s, 1H), 5.33 (s, 1H), 4.48 (dd, 1H), 4.30 (s, 1H), 4.03 (dd, 2H), 3.83 (t, 2H), 3.14 (d, 1H), 2.82 (dd, 2H), 2.40-2.09 (m, 6H), 2.10-1.61 (m, 7H), 1.50-1.21 (m, 5H), 0.77 (s, 3H).

EXAMPLE 18

(1R,3aS,3bS,10aR,10bS,11S,12aS)-7-(4-Fluorophenyl)-11-hydroxy-1-{[(2-hydroxyethyl)sulfanyl]carbonyl}-10a,12a-dimethyl-1,2,3,3a,3b,4,5,7,10,10a,10b,11,12,12a-tetradecahydrocyclopenta[5,6]naphtho[1,2-f]indazol-1-yl (S)/(R) tetrahydrofuran-2-carboxylate

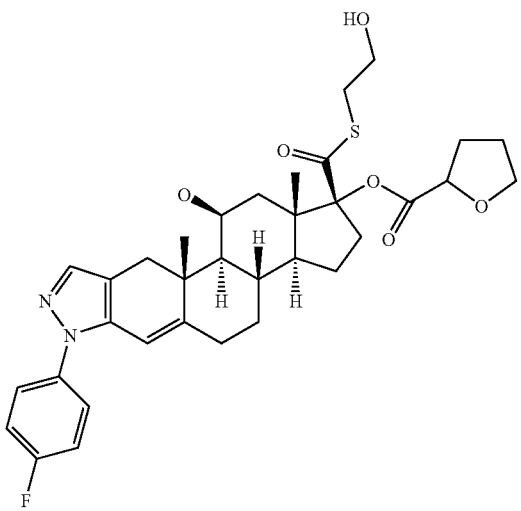

The compound was prepared from Intermediate 29 and 2-bromoethanol according to the procedure described in Example 12. The obtained isomer was the second eluting on a Kromasil C18 HPLC column. APCI-MS m/z: 625 [MH$^+$].
$^1$H NMR (400 MHz, DMSO-d$_6$) δ 7.52 (m, 2H), 7.49 (s, 1H), 7.35 (m, 2H), 6.15 (s, 1H), 4.46 (m, 2H), 4.36 (d, 1H), 3.79 (m, 2H), 3.43 (m, 2H), 2.93 (m, 3H), 2.79 (m, 1H), 2.64 (m, 1H), 2.42 (m, 1H), 2.29 (m, 1H), 2.14 (m, 3H), 2.00-1.70 (m, 7H), 1.58 (m, 1H), 1.34 (m, 1H), 1.22 (s, 3H), 1.11 (m, 1H) 1.00 (m, 1H), 0.86 (s, 3H). APCI-MS m/z: 625 [MH$^+$].

EXAMPLE 19

(1R,3aS,3bS,10aS,10bR,11S,12aS)-1-{[Cyanomethyloxy]carbonyl}-10b-fluoro-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate

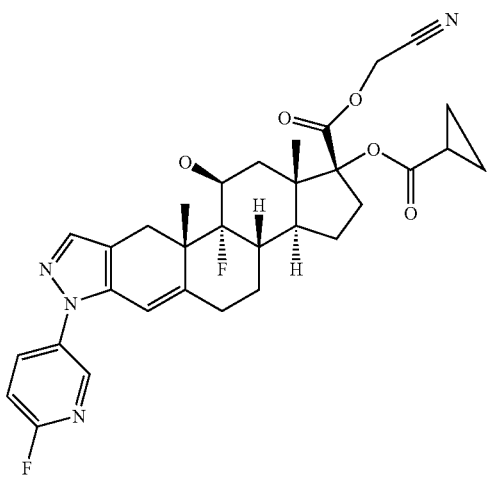

The compound was prepared according to the procedure for Example 12 starting from Intermediate 30 and 2-Bromoacetonitrile. APCI-MS m/z: 554 [MH$^+$].
$^1$H NMR (400 MHz, DMSO) δ 8.40 (d, 1H), 8.15 (d, 1H), 7.57 (s, 1H), 7.36 (dd, 1H), 6.25 (s, 1H), 5.24 (s, 1H), 5.02 (dd, 2H), 4.25 (d, 1H), 3.14 (d, 1H), 2.88-2.64 (m, 2H), 2.41-1.99 (m, 5H), 1.82-1.57 (m, 5H), 1.50-1.36 (m, 2H), 1.33 (s, 3H), 0.95 (s, 3H), 0.88-0.75 (m, 4H).

EXAMPLE 20

(1R,3aS,3bS,10aS,10bR,11S,12aS)-1-{[Cyanomethyloxy]carbonyl}-7-(6-fluoropyridin-3-yl)-11-hydroxy-10a,12a-dimethyl-1,2,3,3a,3b,4,5,7,10,10a,10b,11,12,12a-tetradecahydrocyclopenta[5,6]naphtho[1,2-f]indazol-1-yl cyclopropanecarboxylate

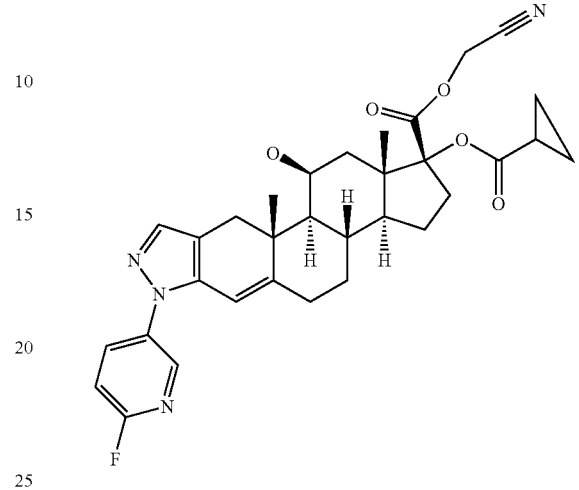

The compound was prepared according to the procedure for Example 12, starting from Intermediate 31 and 2-Bromoacetonitrile. APCI-MS m/z: 575 [MH$^+$].
$^1$H NMR (400 MHz, DMSO) δ 8.39 (d, 1H), 8.13 (d, 1H), 7.54 (s, 1H), 7.35 (dd, 1H), 6.17 (s, 1H), 5.00 (dd, 2H), 4.42 (s, 1H), 4.35 (d, 1H), 2.97 (d, 1H), 2.85-2.58 (m, 2H), 2.46-2.25 (m, 2H), 1.98-1.81 (m, 3H), 1.81-1.56 (m, 5H), 1.49-1.31 (m, 1H), 1.23 (s, 3H), 1.19-0.98 (m, 2H), 0.96-0.76 (m, 7H).

EXAMPLE 21

(1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate

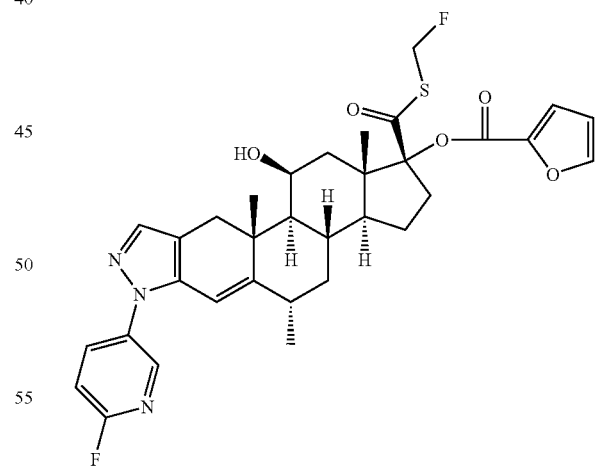

The compound was prepared according to the description in Example 2, starting from intermediate 32. APCI-MS m/z: 624 [MH$^+$].
$^1$H NMR (400 MHz, CDCl$_3$) δ 8.38 (1H, s), 8.01 (1H, m), 7.62 (1H, s), 7.51 (1H, s), 7.23 (1H, m), 7.09 (1H, dd), 6.55 (1H, m), 6.13 (1H, s), 6.09-5.58 (2H, m), 4.64 (1H, bs), 3.16-3.00 (2H, m), 2.82 (1H, d), 2.55 (1H, bs), 2.28 (1H, d), 2.21-2.05 (3H, m), 1.97 (1H, m), 1.92-1.80 (1H, m), 1.80-1.68 (1H, m), 1.60-1.46 (1H, m), 1.37 (3H, s), 1.33 (1H, d), 1.17-1.13 (1H, m), 1.12 (3H, d), 1.06 (3H, s), 0.90 (1H, q).

EXAMPLE 22

(1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl furan-2-carboxylate

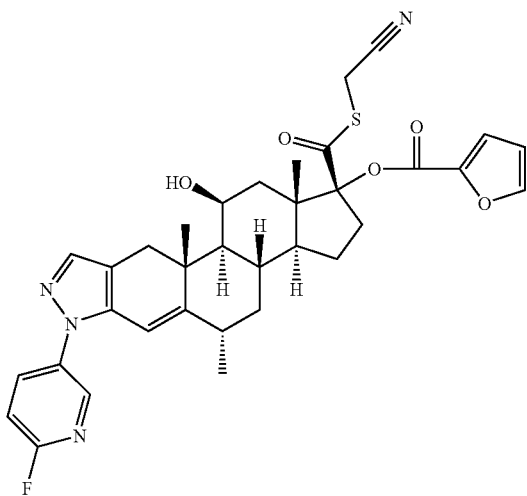

The compound was prepared according to the description in Example 3, starting from intermediate 32. APCI-MS m/z: 631 [MH$^+$].

$^1$H NMR (400 MHz, CDCl$_3$) δ 8.37 (1H, s), 8.01 (1H, m), 7.63 (1H, s), 7.51 (1H, s), 7.23 (1H, m), 7.09 (1H, dd), 6.55 (1H, m), 6.12 (1H, s), 4.64 (1H, bs), 3.82 (1H, d, AB), 3.55 (1H, d, AB), 3.13-3.01 (2H, m), 2.82 (1H, d), 2.56 (1H, bs), 2.25 (1H, d), 2.21-2.10 (2H, m), 2.06 (1H, d), 1.97 (1H, m), 1.92-1.80 (1H, m), 1.80-1.67 (1H, m), 1.59-1.48 (1H, m), 1.36 (3H, s), 1.32 (1H, d), 1.23-1.19 (1H, m), 1.12 (3H, d), 1.07 (3H, s), 0.89 (1H, q).

EXAMPLE 23

(1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl propanoate

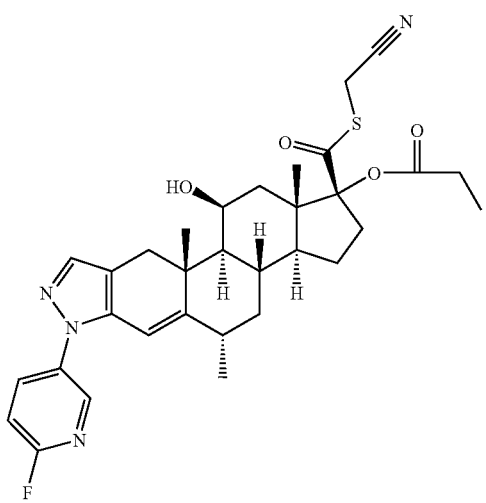

The compound was prepared according to the description in Example 3, starting from intermediate 14. APCI-MS m/z: 593 [MH$^+$].

$^1$H NMR (400 MHz, CDCl$_3$) δ 8.37 (1H, s), 8.01 (1H, m), 7.50 (1H, s), 7.09 (1H, dd), 6.12 (1H, s), 4.57 (1H, bs), 3.79 (1H, d, AB), 3.56 (1H, d, AB), 3.06-2.92 (2H, m), 2.77 (1H, d), 2.54 (1H, bs), 2.37 (2H, q), 2.18-2.06 (2H, m), 2.03-1.91 (3H, m), 1.89-1.76 (1H, m), 1.67-1.55 (1H, m), 1.54-1.41 (1H, m), 1.34 (3H, s), 1.26 (1H, d), 1.20-1.09 (7H, m), 1.01 (3H, s), 0.86 (1H, q).

EXAMPLE 24

(1R,3aS,3bS,5S,10aR,10bS,11S,12aS)-1-{[(Cyanomethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate

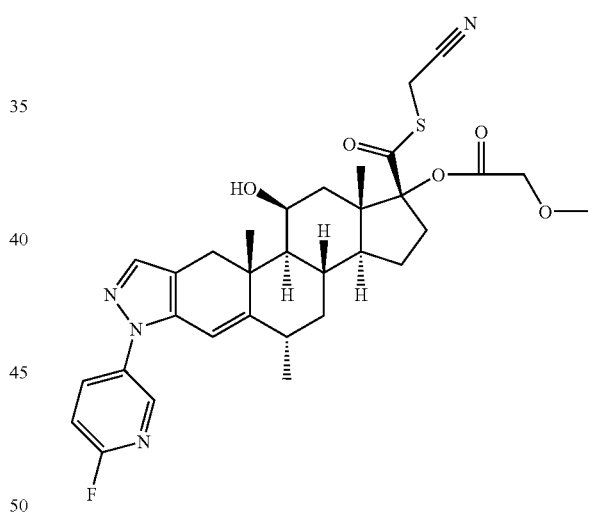

The compound was prepared according to the description in Example 3, starting from intermediate 15. APCI-MS m/z: 609 [MH$^+$].

$^1$H NMR (400 MHz, CDCl$_3$) δ 8.36 (1H, s), 8.01 (1H, m), 7.49 (1H, s), 7.09 (1H, dd), 6.12 (1H, s), 4.57 (1H, bs), 4.06 (2H, s), 3.79 (1H, d, AB), 3.58 (1H, d, AB), 3.46 (3H, s), 3.07-2.95 (2H, m), 2.77 (1H, d), 2.54 (1H, bs), 2.19-2.00 (3H, m), 2.00-1.91 (2H, m), 1.88-1.77 (1H, m), 1.67-1.43 (2H, m), 1.34 (3H, s), 1.25 (1H, d), 1.17 (1H, d), 1.12 (3H, d), 1.02 (3H, s), 0.86 (1H, q).

EXAMPLE 25

(1R,3aS,3bS,5S,10aR,10bS,11S,12aS)-1-{[(Fluoromethyl)sulfanyl]carbonyl}-7-(6-fluoropyridin-3-yl)-11-hydroxy-5,10a,12a-trimethyl-1,2,3,3a,3b,4,5,7,10,10a,10b,11,12,12a-tetradecahydrocyclopenta[5,6]naphtho[1,2-f]indazol-1-yl cyclopropanecarboxylate

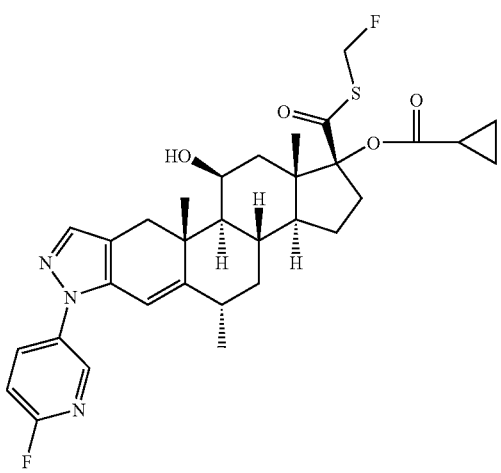

The compound was prepared according to the description in Example 2, starting from intermediate 17. APCI-MS m/z: 598 [MH+].

$^1$H NMR (400 MHz, CDCl$_3$) δ 8.37 (1H, s), 8.01 (1H, m), 7.49 (1H, s), 7.09 (1H, dd), 6.12 (1H, s), 6.05-5.60 (2H, m), 4.58 (1H, bs), 3.07-2.93 (2H, m), 2.77 (1H, d), 2.54 (1H, bs), 2.19-2.06 (2H, m), 2.05-1.90 (3H, m), 1.90-1.78 (1H, m), 1.72-1.60 (2H, m), 1.52-1.40 (1H, m), 1.34 (3H, s), 1.27 (1H, d), 1.16-1.09 (4H, m), 1.08-0.98 (5H, m), 0.96-0.83 (3H, m).

EXAMPLE 26

(1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl propanoate

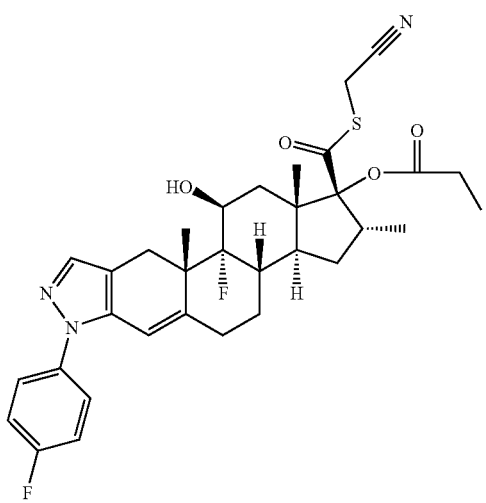

The compound was prepared from intermediate 8, according to the preparation described in Example 5. APCI-MS m/z: 610 [MH+].

$^1$H NMR (400 MHz, CDCl$_3$) δ 7.50-7.43 (3H, m), 7.16 (2H, t), 6.17 (1H, s), 4.45 (1H, bs), 3.72 (2H, s), 3.40-3.26 (2H, m), 2.79 (1H, d), 2.59 (1H, t), 2.49-2.38 (3H, m), 2.38-2.18 (3H, m), 1.94-1.81 (2H, m), 1.75-1.64 (1H, m), 1.63-1.51 (1H, m), 1.40 (3H, s), 1.38-1.33 (2H, m), 1.16 (3H, t), 1.12 (3H, s), 1.01 (3H, d).

EXAMPLE 27

(1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate

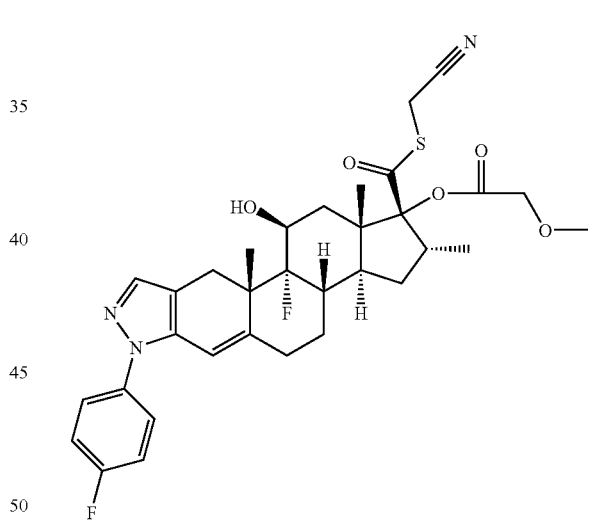

The compound was prepared from intermediate 8, according to the procedure described in Example 6. APCI-MS m/z: 626 [MH+].

$^1$H NMR (400 MHz, CDCl$_3$) δ 7.50-7.42 (3H, m), 7.16 (2H, t), 6.18 (1H, s), 4.46 (1H, bs), 4.12 (2H, s), 3.73 (2H, s), 3.45 (3H, s), 3.42-3.26 (2H, m), 2.79 (1H, d), 2.59 (1H, t), 2.45-2.18 (4H, m), 1.95-1.81 (2H, m), 1.75-1.64 (1H, m), 1.63-1.51 (1H, m), 1.40 (3H, s), 1.39-1.32 (2H, m), 1.13 (3H, s), 1.05 (3H, d).

EXAMPLE 28

(1R,2R,3aS,3bS,10aS,10bR,11S,12aS)-10b-Fluoro-1-{[(fluoromethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate

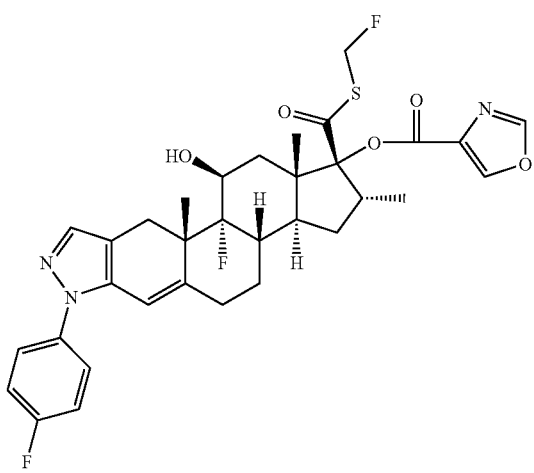

The compound was prepared from intermediate 8, according to the procedure described in Example 6. APCI-MS m/z: 642 [MH+].
$^1$H NMR (400 MHz, CDCl$_3$) δ 8.25 (1H, s), 7.94 (1H, s), 7.50-7.43 (3H, m), 7.17 (2H, t), 6.19 (1H, s), 6.04-5.76 (2H, m), 4.51 (1H, bs), 3.56-3.44 (1H, m), 3.37 (1H, d), 2.81 (1H, d), 2.68-2.50 (2H, m), 2.46-2.25 (3H, m), 2.01-1.85 (2H, m), 1.80-1.68 (1H, m), 1.63-1.51 (1H, m), 1.42 (3H, s), 1.39 (1H, m), 1.33 (1H, bs), 1.17 (3H, s), 1.09 (3H, d).

EXAMPLE 29

(1R,2R,3aS,3bS,10aS,10bR,11S,12aS)-10b-Fluoro-1-{[(cyanomethyl)sulfanyl]carbonyl}-7-(4-fluorophenyl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl 1,3-oxazole-4-carboxylate

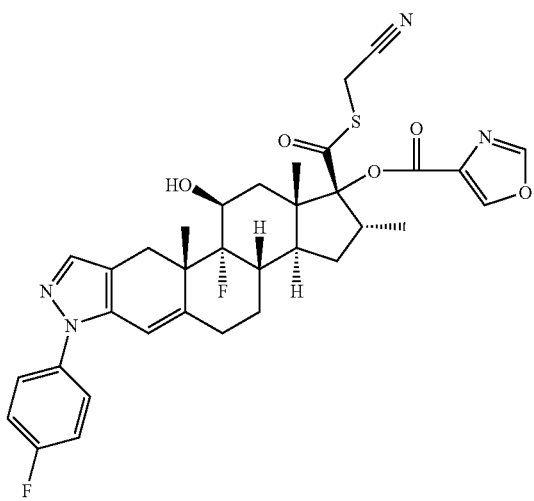

The compound was prepared from intermediate 8, according to the procedure described in Example 6. APCI-MS m/z: 649 [MH+].

EXAMPLE 30

(1R,2R,3aS,3bS,10aS,10bR,11S,12aS)-10b-Fluoro-1-{[(cyanomethyl)sulfanyl]carbonyl}-7-(6-fluoropyridin-3-yl)-11-hydroxy-2,10a,12a-trimethyl-1,2,3,3a,3b,4,5,7,10,10a,10b,11,12,12a-tetradecahydrocyclopenta[5,6]naphtho[1,2-f]indazol-1-yl methoxyacetate

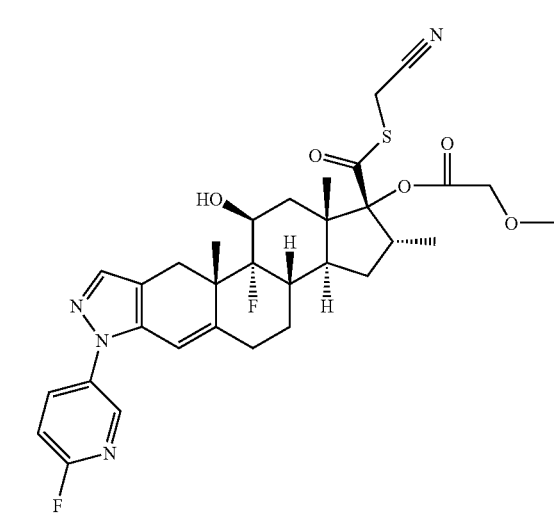

The compound was prepared from intermediate 5, according to the procedure described in Example 1. APCI-MS m/z: 627 [MH+].
$^1$H NMR (400 MHz, CDCl$_3$) δ 8.36 (1H, s), 7.99 (1H, m), 7.51 (1H, s), 7.07 (1H, dd), 6.18 (1H, s), 4.45 (1H, bs), 4.12 (2H, s), 3.73 (2H, s), 3.45 (3H, s), 3.42-3.27 (2H, m), 2.81 (1H, d), 2.61 (1H, t), 2.44-2.32 (2H, m), 2.31-2.18 (2H, m), 1.96-1.82 (2H, m), 1.75-1.66 (1H, m), 1.65-1.51 (1H, m), 1.41 (3H, s), 1.40-1.34 (2H, m), 1.13 (3H, s), 1.05 (3H, d).

Human Glucocorticoid Receptor (GR) Assay

The assay is based on a commercial kit from Panvera/Invitrogen (Part number P2893). The assay technology is fluorescence polarization. The kit utilises recombinant human GR (Panvera, Part number P2812), a Fluoromone™ labelled tracer (GS Red, Panvera, Part number P2894) and a Stabilizing Peptide 10× (Panvera, Part number P2815). The GR and Stabilizing Peptide reagents are stored at −70° C. while the GS Red is stored at −20° C. Also included in the kit are 1M DTT (Panvera, Part number P2325, stored at −20° C.) and GR Screening buffer 10× (Panvera, Part number P2814, stored at −70° C. initially but once thawed stored at room temperature). Avoid repeated freeze/thaws for all reagents. The GR Screening buffer 10× comprises 100 mM potassium phosphate, 200 mM sodium molybdate, 1 mM EDTA and 20% DMSO.

Test compounds (1 μL) and controls (1 μL) in 100% DMSO were added to black is polystyrene 384-well plates (Greiner low volume black flat-bottom, part number 784076). 0% control was 100% DMSO and 100% control was 10 μM Dexamethasone. Background solution (8 μL; assay buffer 10×, Stabilizing Peptide, DTT and ice cold MQ water) was added to the background wells. GS Red solution (7 μL; assay buffer 10×, Stabilizing Peptide, DTT, GS Red and ice cold water) was added to all wells except background wells. GR solution (7 µL; assay buffer 10×, Stabilizing Peptide, DTT, GR and ice cold water) was added to all wells. The plate was sealed and incubated in a dark at room temperature for 2 hours. The plate was read in an Analyst plate reader (LJL Biosystems/Molecular Devices Corporation) or other similar plate reader capable of recording fluorescence polarization (excitation wavelength 530 nm, emission wavelength 590 nm and a dichroic mirror at 561 nm). The $IC_{50}$ values were calculated using XLfit model 205 and are shown in Table 1.

TABLE 1

| Example No. | Inhibition of GR binding, $IC_{50}$ (nM) | Example No. | Inhibition of GR binding, $IC_{50}$ (nM) |
| --- | --- | --- | --- |
| 1 | 3.5 | 2 | 1.9 |
| 3 | 1.6 | 4 | 2.8 |
| 5 | 11 | 6 | 7.8 |
| 7 | 1.9 | 8 | 0.93 |
| 9 | 1.5 | 10 | 0.89 |
| 11 | 2.1 | 12 | 1 |
| 13 | 0.98 | 14 | 0.65 |
| 15 | 0.55 (racemate) 0.57 (R)/(S) isomer 0.58 (S)/(R) isomer | 16 | 0.53 (racemate) 0.44 (R)/(S) isomer 1.3 (S)/(R) isomer |
| 17 | 0.55 | 18 | 3.1 |
| 19 | 1.4 | 20 | 2.3 |
| 21 | 2.8 | 22 | 1.7 |
| 23 | 1 | 24 | 1.1 |
| 25 | 1.2 | 26 | 17 |
| 27 | 6 | 28 | 15 |
| 29 | 5.5 | 30 | 1.6 |

The invention claimed is:

1. A compound having the following formula:

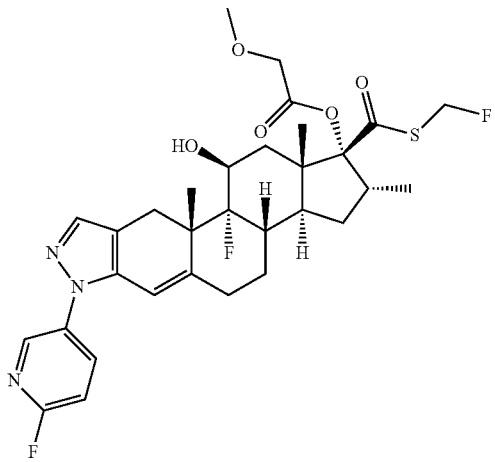

or a pharmaceutically acceptable salt thereof.

2. A pharmaceutical composition comprising the compound of claim 1 or a pharmaceutically acceptable salt thereof in association with a pharmaceutically acceptable adjuvant, diluent or carrier.

3. A pharmaceutical combination comprising the compound of claim 1 or a pharmaceutically acceptable salt thereof, one or more agents independently selected from:
   a selective $\beta_2$ adrenoreceptor agonist;
   a phosphodiesterase inhibitor;
   a protease inhibitor;
   an anticholinergic agent;
   a modulator of chemokine receptor function; and
   an inhibitor of kinase function;
   and optionally one or more pharmaceutically acceptable excipients.

4. A kit comprising a preparation of a first active ingredient which is the compound of claim 1 or a pharmaceutically acceptable salt thereof, and a preparation of a second active ingredient which is
   a selective $\beta_2$ adrenoreceptor agonist;
   a phosphodiesterase inhibitor;
   a protease inhibitor;
   an anticholinergic agent;
   a modulator of chemokine receptor function; or
   an inhibitor of kinase function;
   and instructions for the simultaneous, sequential or separate administration of the preparations to a patient in need thereof.

5. A method of treating, or reducing the risk of, asthma comprising administering to a patient in need thereof a therapeutically effective amount of the compound of claim 1 or a pharmaceutically acceptable salt thereof.

6. A method of treating, or reducing the risk of, chronic obstructive pulmonary disease comprising administering to a patient in need thereof a therapeutically effective amount of the compound of claim 1 or a pharmaceutically acceptable salt thereof.

7. A process for preparing the pharmaceutical composition of claim 2, comprising mixing the compound of claim 1 or a pharmaceutically acceptable salt thereof with a pharmaceutically acceptable adjuvant, diiluent, or carrier.

* * * * *